(12) United States Patent
Dvorak

(10) Patent No.: US 8,470,177 B2
(45) Date of Patent: Jun. 25, 2013

(54) METHOD AND APPARATUS FOR ANAEROBIC DIGESTION OF ORGANIC LIQUID WASTE STREAMS

(75) Inventor: Stephen W. Dvorak, Chilton, WI (US)

(73) Assignee: DVO Licensing, Inc., Chilton, WI (US)

( * ) Notice: Subject to any disclaimer, the term of this patent is extended or adjusted under 35 U.S.C. 154(b) by 759 days.

(21) Appl. No.: 12/516,104

(22) PCT Filed: Nov. 27, 2006

(86) PCT No.: PCT/US2006/061252
§ 371 (c)(1),
(2), (4) Date: Feb. 24, 2010

(87) PCT Pub. No.: WO2008/066546
PCT Pub. Date: Jun. 5, 2008

(65) Prior Publication Data
US 2010/0140169 A1    Jun. 10, 2010

(51) Int. Cl.
*C02F 3/28* (2006.01)
*C02F 11/04* (2006.01)
(52) U.S. Cl.
USPC ............ 210/603; 210/613; 210/614; 210/259
(58) Field of Classification Search
USPC ................ 210/603, 612, 613, 614, 143, 252, 210/259
See application file for complete search history.

(56) References Cited

U.S. PATENT DOCUMENTS 2,893,957 A * 7/1959 Kennedy et al. ............. 210/603
3,845,939 A   11/1974 Waldenville
4,022,665 A   5/1977 Ghosh et al.
4,057,401 A   11/1977 Boblitz
4,100,023 A   7/1978 McDonald
4,133,273 A   1/1979 Glennon
4,209,303 A   6/1980 Ricks
(Continued)

FOREIGN PATENT DOCUMENTS

EP    0213691 A2    3/1987
EP    0213691 A2    11/1987
(Continued)

OTHER PUBLICATIONS

Wilke, A.; Anaerobic Treatment of Agricultural Wastes, "Dairy Waste Fixed Film Digester Design Example," presentation, no date, 10 pgs.

(Continued)

*Primary Examiner* — Fred Prince
(74) *Attorney, Agent, or Firm* — Whyte Hirschboeck Dudek S.C.

(57) ABSTRACT

A system and method for treating high-strength organic liquid waste. Generally, the method includes feeding influent high-strength organic liquid waste including organic molecules to an anaerobic digester, converting at least a portion of the organic molecules in the liquid waste to acids using acid forming bacteria, converting at least a portion of the acids in the liquid waste to methane using methanogenic bacteria, separating the liquid waste after treatment with the methanogenic bacteria into alkaline sludge and effluent, and using the alkaline sludge to adjust the pH of the liquid waste in the anaerobic digester. In the case of acidic high-strength organic liquid wastes, a portion of the acids produced by the acid forming bacteria may be recirculated to the front of the anaerobic digester and combined with influent high-strength organic liquid waste.

67 Claims, 9 Drawing Sheets

U.S. PATENT DOCUMENTS

| | | | |
|---|---|---|---|
| 4,213,857 A | 7/1980 | Ishida et al. | |
| 4,230,580 A | 10/1980 | Dodson | |
| 4,246,099 A | 1/1981 | Gould et al. | |
| 4,252,901 A | 2/1981 | Fischer et al. | |
| 4,274,838 A | 6/1981 | Dale et al. | |
| 4,289,625 A | 9/1981 | Tarman et al. | |
| 4,323,367 A | 4/1982 | Ghosh | |
| 4,342,836 A | 8/1982 | Harvey | |
| 4,354,936 A | 10/1982 | Ishida et al. | |
| 4,436,817 A | 3/1984 | Nemetz | |
| 4,442,006 A | 4/1984 | Ishida et al. | |
| 4,521,310 A | 6/1985 | Casey | |
| 4,522,721 A | 6/1985 | Ishida et al. | |
| 4,551,243 A | 11/1985 | Martin | |
| 4,568,457 A | 2/1986 | Sullivan | |
| 4,735,724 A | 4/1988 | Chynoweth et al. | |
| 4,750,454 A | 6/1988 | Santina et al. | |
| 4,780,415 A | 10/1988 | Ducellier et al. | |
| 4,798,802 A | 1/1989 | Ryan | |
| 4,857,458 A | 8/1989 | Nobilet et al. | |
| 5,091,315 A | 2/1992 | McCarty et al. | |
| 5,207,911 A | 5/1993 | Pellegrin et al. | |
| 5,409,610 A | 4/1995 | Clark | |
| 5,453,376 A | 9/1995 | Ek | |
| 5,496,730 A | 3/1996 | Teramachi | |
| 5,527,464 A | 6/1996 | Bartha et al. | |
| 5,587,320 A | 12/1996 | Shindo et al. | |
| 5,593,590 A | 1/1997 | Steyskal | |
| 5,637,219 A | 6/1997 | Robinson et al. | |
| 5,672,506 A | 9/1997 | Aoyagi et al. | |
| 5,710,062 A | 1/1998 | Shindo et al. | |
| 5,772,887 A | 6/1998 | Noah et al. | |
| 6,048,458 A | 4/2000 | Vogt et al. | |
| 6,087,155 A | 7/2000 | York et al. | |
| 6,103,191 A | 8/2000 | Luker | |
| 6,139,744 A | 10/2000 | Spears et al. | |
| 6,168,642 B1 | 1/2001 | Valkanas et al. | |
| 6,254,775 B1 | 7/2001 | McElvaney | |
| 6,299,744 B1 | 10/2001 | Narayanan et al. | |
| 6,342,378 B1 | 1/2002 | Zhang et al. | |
| 6,410,283 B1 | 6/2002 | Rehmat et al. | |
| 6,451,589 B1 | 9/2002 | Dvorak | |
| 6,521,129 B1 | 2/2003 | Stamper et al. | |
| 6,551,510 B1 | 4/2003 | Bakke et al. | |
| 6,613,562 B2 | 9/2003 | Dvorak | |
| 6,663,777 B2 | 12/2003 | Schimel | |
| 6,673,243 B2 | 1/2004 | Srinivasan et al. | |
| 6,824,682 B2 | 11/2004 | Branson | |
| 6,855,253 B2 | 2/2005 | Baumgartner et al. | |
| 6,929,744 B2 | 8/2005 | Le | |
| 6,982,035 B1 | 1/2006 | O'Keefe | |
| 6,984,305 B2 | 1/2006 | McAlister | |
| 7,078,229 B2 | 7/2006 | Dvorak | |
| 7,179,642 B2 | 2/2007 | Dvorak | |

FOREIGN PATENT DOCUMENTS

| | | | |
|---|---|---|---|
| EP | 1081100 | 7/2001 | |
| GB | 1561573 | 2/1980 | |
| JP | 10225674 | 8/1998 | |
| JP | 11104601 | 4/1999 | |
| WO | 2008066508 A1 | 6/2008 | |
| WO | 2008066546 A1 | 6/2008 | |
| WO | 2008140986 A1 | 11/2008 | |

OTHER PUBLICATIONS

Wilkie, A.; Anaerobic Digestion: Holistic Bioprocessing of Animal Manures; no date, 15 pgs, Soil and Water Science Depart, University of Florida, Gainsville, FL USA.

Williams, C.; The Feasibility of Thermophilic Anaerobic Digestion for Treating Animal Wastes; no date, 10 pgs, Animal & Poultry Waste Management Center; North Carolina State University, Raleigh, NC USA.

Williams, C. et al; Baseball Stadium Hits Home Run for Recycling and Composting, magazine, Feb. 2005, p. 56, BioCycle.

Witherspoon, J. et al; Public Enemy No. 1 for Biosolids, magazine, May 2004, pp. 31-35, WE&T.

Wright, P.; Anaerobic Treatment of Agricultural Wastes, "Design & Operational Considerations (Part 1)," presentation, no date, 17 pgs.

Wright, P.; Anaerobic Treatment of Agricultural Wastes, "Design & Operational Considerations (Part 2)," presentation, no date, 24 pgs.

Wright, P.; An Economic Comparison of Two Anaerobic Digestion Systems on Dairy Farms, presentation, Jul. 27-30, 2003, 7 pgs, 2003 ASAE Annual International Meeting, Las Vegas, Nevada, USA.

Wright, P.; Anaerobic Treatment of Agricultural Wastes, "Dairy Plug Flow Digester Design Example," presentation, no date, 18 pgs.

Yen, H et al; Anaerobic co-digestion of algal sludge and waste paper to produce methane, available online Jan. 4, 2006, 1 pg, from website: ScienceDirect—Bioresource Technology.

PCT International Search Report mailed Mar. 12, 2007 for PCT/US06/45414 filed on Nov. 27, 2006.

PCT International Preliminary Report on Patentability Written Opinion of the International Search Authority mailed Jun. 3, 2009 for PCT/US06/45414 filed on Nov. 27, 2006.

PCT International Search Report mailed Oct. 1, 2007 for PCT/US2006/61252 filed on Nov. 27, 2006.

PCT International Preliminary Report on Patentability Written Opinion of the International Searching Authority mailed Jun. 3, 2009 for PCT/US2006/61252 filed on Nov. 27, 2006.

PCT International Search Report mailed Oct. 10, 2008 for PCT/US2008/062624 filed on Oct. 10, 2008.

PCT International Preliminary Report on Patentability Written Opinion of the International Searching Authority mailed Nov. 10, 2009 for PCT/US2008/062624 filed on May 5, 2008.

A Centralised Thermophilic Biogas Plant in Denmark; Tech Brochure #43; 1996; 4 pgs, CADDET; United Kingdom.

A Long History of Digesters that Work, newsletter, Sep. 2004, RCM Digesters, Inc., Berkeley, CA, USA.

Agricultural Waste Characteristics; Agricultural Waste Management Field Handbook, 1992, Chapter 4, pp. 1-12; and Anaerobic Digester Technology Application in Animal Agriculture, Jul. 1996, Chapter 10, pp. 72-77 (17 pgs).

Allan, D. et al; Fertilizer Value and Weed Seed Destruction Potential of Digested Manure, presentation, Jun. 2-4, 2003, 12 pgs.

Alleman, J.; Thermophilic Aerobic Processing of Animal Waste Streams, presentation, Nov. 14-16, 1999, 2 pgs, WEF Animal Residuals Conference.

Alternative Technologies/Uses for Manure; draft, no date, pp. 1-35, EPA.

Amon, B. et al; Greenhouse gas and ammonia emission abatement by slurry treatment, publication, International Congress Series 1293 (2006) pp. 295-298 Elsevier, B.V.

Amon, T. et al; Biogas production from maize and dairy cattle manure—Influence of biomass composition on the methane yield, abstract, available online Jun. 27, 2006, 2 pgs, from website ScienceDirect.

Anaerobic Digester—Ambient Temperature, Code 365, Sep. 2003, NRCS, NHCP.

Anaerobic Digester at Freund Dairy in East Canaan, CT: A Case study, Oct. 21, 2003, 12 pgs. University of Connecticut Cooperative Extension System (article contains references from 1997).

Anaerobic Digesters; printed May 31, 2007, 2 pgs, Alliant Energy, from website: http://www.alliant energy.com/docs/groups/public/documents/pub/p014727.hcsp?print=true.

Anaerobic Digestion of Farm Waste in the UK; Technical Brochure No. 60, 1997, 4 pgs, CADDET; United Kingdom.

Anaerobic digestion of Piggery Wastes in Victoria, Australia; Technical Brochure No. 4, 1994, 4 pgs, CADDET.

Anaerobic digestion, printed Nov. 8, 2006, 4 pgs, from website: http://www.btgworld.com/technologies/anaerobic-digestion.html.

Anaerobic Systems in Washington State, "Digesters Bring Power and Income to West Coast Dairy Farms," magazine, Nov. 2004, pp. 54-55, Biocycle.

Anaerobic Treatment of Agricultural Wastes, presentation contents sheet, Nov. 3-5, 2003, 1 pg, NRCS, Nashville, Tennessee, USA.

Angelidaki, I. et al; Thermophilic anaerobic digestion of livestock waste: the effect of ammonia, publication, 1993, 38:560-564, Appl. Microbiol Biotechnology, Denmark.

Appendix V: Supporting Material for the Analysis of Livestock Manure Management; Sep. 1999, pp. V1-7 and p. 5-17, U.S. EPA.

Balsam, J.; Anaerobic Digestion of Animal Wastes: Factors to Consider, electronic newsletter, Oct. 2002, pp. 1-12, ATTRA, operated by NCT.

Biomass Gasifier System, printed Dec. 12, 2006, 4 pgs, Goodrich World, from website: http://www.goodrichworld.com/Biomass-gasifier-system.html.

Blume, E.; Manure Produces Power, magazine, Jul./Aug. 2005, 2 pgs, Engineering Professional.

Boersma, L. et al.; Methods for the Recovery of Nutrients and Energy from Swine Manure, 1981, pp. 3-14, Neth. J. Agric. Science 29.

Bogovich, W. et al; Long Term Operation and Maintenance of a Digester at the Brendle Farms Poultry Operation, presentation, Aug. 1-4, 2004, pp. 1-8, Ontario, Canada, 2004 ASAE/CSAE Annual International Meeting.

Burns, R. et al; Laboratory and In-Situ Reductions of Soluble Phosphorus in Liquid Swine Waste Slurries, printed Apr. 17, 2003, 3 pgs, UT Animal Waste Management, from website: http://wastemgmt.ag.utk.edu/struvite_2.htm.

Burns, R. et al; Phosphorus Recovery from Animal Manures using Optimized Struvite Precipitation, published in Proceedings of Coagulants and Flocculants: Global Market and Technical Opportunities for Water Treatment Chemicals May 22-24, 2002, pp. 1-7, Chicago, IL.

Burns, R.; Anaerobic Treatment of Agricultural Wastes, "Anaerobic Treatment System Configurations," presentation, no date, 16 pgs, University of Tennessee Institute of Agriculture.

Cheng, J et al; Final Report to Dr. C. Mike Williams, Director, NCSU Animal and Poultry Waste Management Center, report, May 20, 2004, 30 pgs.

Cicek, N.; A review of membrane bioreactors and their potential application in the treatment of agricultural wastewater, publication, 2003, vol. 45, pp. 6.37-6.49, Canadian Biosystems Engineering, Manitoba, Canada.

Cleveland, A.; Final report on the use of a bioremediation system on a sewage lagoon at a Dept. of Defense Facility, Nov. 2000, 4 pgs.

Control of Pathogens and Vector Attraction in Sewage Sludge, Oct. 1999, 6 pgs, EPA/6251R-92/013.

Crooks, A; Protecting Forests and Supporting Renewable Energy, magazine, Apr. 2005, vol. 46, No., p. 68 4. pgs. printed from website http://www.jgpress.com/archives/_free/000411.html,BioCycle.

DeLuna, J.; Understanding the Hazards of Flame Retardants—Polybrominated diphenyl ethers are becoming more prevalent with unknown long-term effects on humans, magazine, 2003, vol. 15, No. 8, p. 74, Water Environment and Technology (WE&T).

Demirer, G; Effect of retention time and organic loading rate on anaerobic acidification and biogasification of dairy manure abstract, research article accepted: Jul. 8, 2004, 1 pg, from website: Wiley Interscience: Journal: Abstract, Publication Date Sep. 2004.

Digester biochemistry, no date, 1 pg, from website: bungah@rpi.edu.

Digestive Enzyme Facts, printed Dec. 12, 2006, 3 pgs, Beta Force; from website: http://www.beta-glucan-info.com/digestive_enyme_facts.htm.

Dvorak, M.; Improving Herd Health, "Digester Provides Power and Cow Comfort," magazine, Aug. 2005, p. 47, Biocycle.

Dvorak, S.; Anaerobic Treatment of Agricultural Wastes, "Dairy Waste Digester Design Example," presentation, no date, 10 pgs.

Dvorak, S.; Progress in Anaerobic Digesters, "New Markets for Recycled Bedding From Digesters," magazine, Oct. 2004, p. 44, Biocycle.

Emission and reduction of greenhouse gases from agriculture and food manufacturing, report, Dec. 1999, 41 pgs., USDOE.

EPA may target carbon dioxide; newspaper, Feb. 28, 2001, 1 pg, Milwaukee Journal Sentinel, Milwaukee, WI.

Erwin, M.; Iowa Swine Producers Views on CSTR Digester, power point presentation, no date, 5 pgs.

Executive Summary Highlights High Solids Anaerobic Digestion Demonstration/Validation, highlights from report, Dec. 10, 2003, 4 pgs, Orbit LLC.

Farm-Based Anaerobic Digestion Practices in the U.S.; printed Jan. 17, 2001, 6 pgs, from website: biogasworks.com.

Fedler, C.; Increasing Technical Support, "Recycling Water Saves Future Drinking Supplies," magazine, Feb. 2005, pp. 50-55, Biocycle.

Fee, R.; Common sense could help solve our growing phosphorus problem; magazine, Feb. 2000, p. 31, Successful Farming.

Ford, J., Steve Dvorak, "Dairy Waste Digester Design Example"; Anaerobic Treatment of Animal Wastes Course Agenda, presentation, Nov. 3-5, 2003, 6 pgs, Nashville, Tennessee, USA.

Foster, R.; An Integrated Anaerobic Digester, Power Generation, Composting System in Operation for Twenty-One Years, presentation, no date, 8 pgs.

Foster, R.; Anaerobic Treatment of Agricultural Wastes, "Dairy Producer/Digester Experience," presentation, no date, 16 pgs.

Fronek, S. et al; Changes, "A Plant modifies its conventional mesophilic digesters to a TPAD system for better quality biosolids," magazine, May 2004, pp. 27-30, WE&T.

Unicom Distributed Energy, The Next Generation of Power brochure, 2 pgs.

Non-Final Office Action mailed Jul. 1, 2010 for U.S. Appl. No. 11/563,574, filed Nov. 27, 2006.

Ghd's Steve Dvorak: Farming Biopower from Manure, quarterly magazine, Winter 2004, pp. 6-7, The Renewable Quarterly.

Goodrich, P.; Anaerobic Digester Systems for Mid-Sized Dairy Farms; report, no date, 45 pgs, AgSTAR Fund for Rural America, The Minnesota Project; Minnesota.

Greer, D.; Creating Cellulosic Ethanol, "Spinning Straw Into Fuel," magazine, Apr. 2005, pp. 61-67, Biocycle.

Han, Y. et al; Temperature-phased anaerobic digestion of wastewater sludges; 1997, vol. 36, No. 6-7, pp. 367-374, Wat. Sci. Tech., Great Britain.

Hanaki, K. et al; Mechanism of inhibition caused by long-chain fatty acids in anaerobic digestion process; 1981, vol. XXIII, pp. 1591-1610, Biotechnology and Bioengineering.

Hansen, C.; Anaerobic Treatment of Agricultural Wastes, "Swine Waste Mixed Flow Digester Design Example," presentation, no date, 17 pgs.

Hansen, R.; Methane Generation From Livestock Wastes, fact sheets, printed Jul. 10, 2003, 6 pgs, Colorado State Univ. Cooperative Extension, from website: http://www.ext.colostate.edu/pubs/farmmgt/05002.html.

Hanusa, D.; Anaerobic Treatment of Agricultural Wastes, "Biogas Handling & Use," presentation, no date, 17 pgs.

Harlow, S.; A dairy goes on the grid, magazine, May 2005, 3 pgs, Environment, reprinted w/permission from Northeast DairyBusiness.

Harrison, J. et al; Evaluation of the pathogen reduction from plug flow and continuous feed anaerobic digesters, article, no date, 6 pgs.

Harrison, J.; Anaerobic digesters & pathogens?, publication, no date, 1 pg, vol. 14, No. 1, WSE Dairy News.

Hoenig, S.; Anaerobic Digestion "A new way to handle manure," magazine, Mar. 1998, 2 pgs, Resource.

Hoff, M.; Final Report, Matt Hoff—Methane Digestion and Composting Feasibility Study, report, Jan. 2006, 70 pgs, EA Engineering, Science and Technology, Inc.

Holmberg, W. et al; Integrated farm energy systems: Building a better biorefinery, printed Jan. 24, 2001, 10 pgs, from website: www.biogasworks.com/reports.

Hopps, D. et al; Yakima Valley Dairy Manure Conversion Project, "USDA Value Added Producer Grant Program," feasibility study, Jan. 2006, 46 pgs.

How the Biocoil Works—The Biocoil Operations Manual, printed Apr. 7, 2005, 2 pgs, from website: http://www.cscadehs.csd.k12.id.us/advbio/95-96/biomanual.html.

Humic Acid/Substances, printed Dec. 12, 2006, 3 pgs, Goodrich World, from website: http://www.goodrichworld.com/humic-acid-substances.html.

Humifulvate® A Natural Active Ingredient, article, printed Dec. 26, 2006, 7 pgs, from website: http://www.enerex.ca/articles/some_humifulvate_science.htm.

Hwu, C. et al; Biosorption of longchain fatty acids in UASB treatment process; publication, 1998, vol. 32, No. 5, pp. 1571-1579, Wat. Res., Great Britain.

Idaho Dairy Waste Conversion to Electricity—A Pilot Project Feasibility Study, Final Report, Oct. 2004, 87 pgs.

Introduction to Anaerobic Digestion, printed Jan. 17, 2001, 2 pgs, from website: http://biogasworks.com/Index/AD%20Intro.htm.

Ito, T. et al; Hydrogen and Ethanol Production from Glycerol-Containing Wastes Discharged after Biodiesel Manufacturing Process, publication, 2005, pp. 260-265, vol. 100, No. 3, Journal of Bioscience and Bioengineering, The Society for Biotechnology, Japan.

Jet Tech "Class A" Auto-thermal thermophilic aerobic digestion (ATAD); 1986, 2 pgs, Jet Tech, Inc. from website.

Jewell, W.; Anaerobic sewage treatment; publication, 1987, pp. 14-21, vol. 21, No. 1, Environ. Sci. Technol.

Johnson, R.; Manure Digester Generates Income, Savings, newspaper, Apr. 3, 2003, 3, pgs, Agri-View.

Journey, W. et al; Anaerobic Enhanced Treatment of Wastewater and Options for Further Treatment; report, Nov. 1996, 95 pgs, ACDI/VOCA; Washington, DC, USA.

Kepp, U. et al; Enhanced stabilization of sewage sludge through thermal hydrolysis—three years of experience with full scale plant; publication, 2000, , vol. 42, No. 9, pp. 89-96, Water Science & Technology.

Keusch, P.; Hard Water Kills Soap, "Objective: The Influence of Hard Water on the Washing Process," Dec. 21, 2006, 2 pgs, from website: http://www.uni-regensburg.de/Fakultaeten/nat_Fak_IV/Organische_Chemie/Didaktik/Keusch/D-hard_water . . . .

Koeslch, R. et al.; Anaerobic Digesters for Dairy Farms, Extension Bulletin 45, no date, 74 pgs, Department of Agricultural and Biological Engineering; New York State College of Agriculture and Life Sciences, Ithaca, NY, USA.

Komiyama, M. et al; Biogas as a reproducible energy source: Its steam reforming for electricity generation and for farm machine fuel, publication, 2006, pp. 234-237, International Congress Series 1293, Elsevier B.V.

Koster, I. et al; Inhibition of Methanogenesis from Acetate in Granular Sludge by Long-Chain Fatty Acids; publication, Feb. 1987, pp. 403-409, Vo.. 53, No. 2, Applied and Environmental Microbiology.

Kramer, J.; Agricultural Biogas Casebook—2004 Update, report, Sep. 2004, 69 pgs.

Krishnan, V. et al; Effect of coagulation on palm oil mill effluent and subsequent treatment of coagulated sludge by anaerobic digestion, publication, (2006), 81:1652-1660, Journal of Chemical Technology and Biotechnology.

Lasonde, W., Drying, burning and creating energy with manure, presentation to Dairy Business Associates , no date, 5 pgs.

Lemley, B., Anything into Oil, May 2003, 9 pgs, Discover vol. 24, No. 5, publication from website: http://www.discovery.com/may_2003/featoil.html.

Leonardite Extract, printed Dec. 12, 2006, 2 pgs, from website: http://www.lgagro.com/HumicAcid.htm.

Lipase—Wikipedia, printed Dec. 12, 2006, 2 pgs, from website: http://en.wkkipedia.org/wiki/Lipase.

Livestock Manure Management; Summary; Sep. 1999, pp. 1-16, Chapter 5, US EPA.

Lorimor, J.; Anaerobic Digestion for 5000 Head Sow Facility, presentation, no date, 14 pgs.

Lorimor, J.; Anaerobic Treatment of Agricultural Wastes, "Dairy Waste Plug Flow Digester Design Examples," presentation, no date, 13 pgs.

Lorimor, J.; Anaerobic Treatment of Agricultural Wastes, "Swine Waste Digester Design Example," presentation, no date, 9 pgs.

Lusk, P., Anaerobic Treatment of Agricultural Wastes, "Economic Considerations for Anaerobic Digestion," presentation, no date, 27 pgs, Resource Development Associates, Pierre, SD, USA.

Lusk, P.; Anaerobic Digestion and Opportunities for International Technology Transfer; magazine, no date, 4 pages, CADDET; United Kingdom.

Lusk, P.; Methane recovery from animal manures: the current opportunities casebook; Sep. 19, 1998, pp. 21-26, Chapter 2, National Energy Renewable Laboratory.

Mackie, R. et al; Anaerobic digestion of cattle waste at mesophilic and thermophilic temperatures, publication, 1995, 43: 346-350, Appl. Microbiol Biotechnol.

Manure Processing Technologies, printed Aug. 5, 2005, 10 pgs, from website: http://res2.agr.gc.ca/initiatives/manurenet/en/man_tech.html, ManureNet, Agriculture and Agri-Food Canada.

Martin, J.; An Evaluation of a Mesophilic, Modified Plug Flow Anaerobic Digester for Dairy Cattle Manure, report, Jul. 20, 2005, 38 pgs, EPA Contract No. GS 10E-0036K, Work Assignment/Task Order No. 9.

Martin, J; A Comparison of Dairy Cattle Manure Management with and without Anaerobic Digestion and Biogas Utilization, report, Mar. 17, 2003, 58 pgs, EPA Contract #68-W7-0068, Task Order 400.

Massart, N. et al; When It Bubbles Over Excessive foam is a symptom of unstable digester conditions, publication, 2006, vol. 18, No. 10 pp. 50-55, Water Environment Federation, USA.

Mattocks, R.; Is a manure digestion system the answer for you?, magazine, Jul./Aug. 2004, pp. 18-23, Manure Manager.

A Manual for Developing Biogas Systems at Commercial Farms in the United States; AgSTAR Handbook; Jul. 1997, EPA.

\* cited by examiner

METHOD AND APPARATUS FOR ANAEROBIC DIGESTION OF ORGANIC LIQUID WASTE STREAMS

BACKGROUND

The anaerobic digestion of organic liquid waste streams has been a fundamental part of waste treatment for hundreds of years. Municipal and industrial wastes have been treated utilizing anaerobic digestion techniques for over 100 years in the United States, and within the last thirty years, anaerobic digestion of higher strength animal wastes has also become an accepted practice. However, a limitation of the bacterial-based anaerobic digestion process has been the inability of anaerobic bacteria to grow outside the parameter of a narrow pH range.

Anaerobic digestion comprises two main classes of anaerobic bacteria: acid forming bacteria (acid formers) and methanogenic bacteria (methane formers). The acid forming bacteria perform best at a pH of about 6.0 to about 7.0 and the methanogenic bacteria perform best at a pH of about 6.5 to about 8.0. These narrow pH ranges preclude effectively utilizing anaerobic digestion waste treatment technology for the treatment of high-strength organic, liquid waste streams having a pH below about 6.5 or above about 8.0.

A high-strength organic liquid waste stream typically has a solids content of about 5% to about 40%. Acidic high-strength organic liquid wastes have a pH of less than about 5.0. Examples of such wastes include acidic cheese whey, with a pH of about 3.5, and the rapidly growing wastes from ethanol plants, with a pH of about 3.5 to about 4.0 and a solids content of about 30% to about 35%. When anaerobic digestion has been attempted with acidic high-strength organic liquid wastes in mixed digesters, the traditional response has been to adjust the pH of the acidic wastes to about 7 with either the addition of expensive chemical pH adjusters or the blending of alkaline waste streams with the acidic wastes. Alkaline high-strength organic liquid wastes have a pH greater than about 8.0. Examples of such wastes include the glycerin by-product waste from biodiesel plants that convert animal oils or vegetable oils into biodiesel. Glycerin typically has a pH of about 12 to about 14 and a high solids content of about 20% to about 35%. When anaerobic digestion has been attempted with alkaline high-strength organic liquid wastes in mixed digesters, the traditional response has been the addition of expensive, corrosive acids, such as sulfuric or citric acids, to lower the pH of the entire digester prior to the anaerobic biodegradation so that the influent pH of the waste stream is continuously adjusted to a pH of about 7.

SUMMARY

In one embodiment, the invention provides a system for treating liquid waste comprising an acid forming chamber that at least partially converts carbon molecules in the liquid waste to acids, a plug-flow methanic chamber downstream from the acid forming chamber that at least partially converts the acids in the liquid waste to methane, a solid-liquid separator downstream from the methanic chamber, the separator separating a portion of the liquid waste into alkaline sludge and effluent, and a first flow path that recycles alkaline sludge to at least one of the acid forming chamber, the methanic chamber, and combination thereof.

In another embodiment, the invention provides a method for treating liquid waste comprising converting carbon molecules within the liquid waste to acids in an acid forming chamber containing acid forming bacteria, converting the acids in the liquid waste from the acid forming chamber into methane in a methanic chamber containing methanogenic bacteria, separating the liquid waste from the methanic chamber into alkaline sludge and effluent, and recycling at least a portion of the alkaline sludge to one of the acid forming chamber, methanic chamber, or combination thereof.

In a further embodiment, the invention provides a closed anaerobic digester for digesting liquid waste, the anaerobic digester comprising a first section positioned to receive liquid waste comprising organic molecules and to convert at least a portion of the carbon molecules within the liquid waste to acids, a second section positioned to receive a portion of the liquid waste from the first section, the second section having one or more walls and converting at least a portion of the acids in the liquid waste to methane, the second section having a first passage and at least one second passage, wherein the waste material changes direction upon flowing from the first passage to the at least one second passage, a third section positioned to receive a portion of the liquid waste from the second section and to separate the liquid waste into an effluent and an alkaline sludge, and a flow path positioned to deliver at least a portion of the alkaline sludge to at least one of the first section, the second section and combination thereof.

In yet a further embodiment, the invention provides a method for treating liquid waste comprising converting carbon molecules within the liquid waste to acids in an acid forming chamber containing acid forming bacteria, wherein the acid forming chamber has a downstream end and an upstream end, recycling at least a portion of the liquid from the downstream end of the acid forming chamber to the upstream end, and converting the acids in the liquid waste from the acid forming chamber into methane in a methanic chamber containing methanogenic bacteria.

In another embodiment, the invention provides a closed anaerobic digester for digesting liquid waste, the anaerobic digester comprising a first section having an upstream end and a downstream end positioned to receive liquid waste comprising organic molecules and to convert at least a portion of the organic molecules within the liquid waste to acids, a second section positioned to receive a portion of the liquid waste from the first section, the second section having one or more walls and converting at least a portion of the acids in the liquid waste to methane, the second section having a first passage and at least one second passage, wherein the waste material changes direction upon flowing from the first passage to the at least one second passage, a third section positioned to receive a portion of the liquid waste from the second section and to separate the liquid waste into an effluent and an alkaline sludge, and a first flow path for recycling liquid waste from the downstream end to the upstream end of the first section.

DETAILED DESCRIPTION

Figure 1:
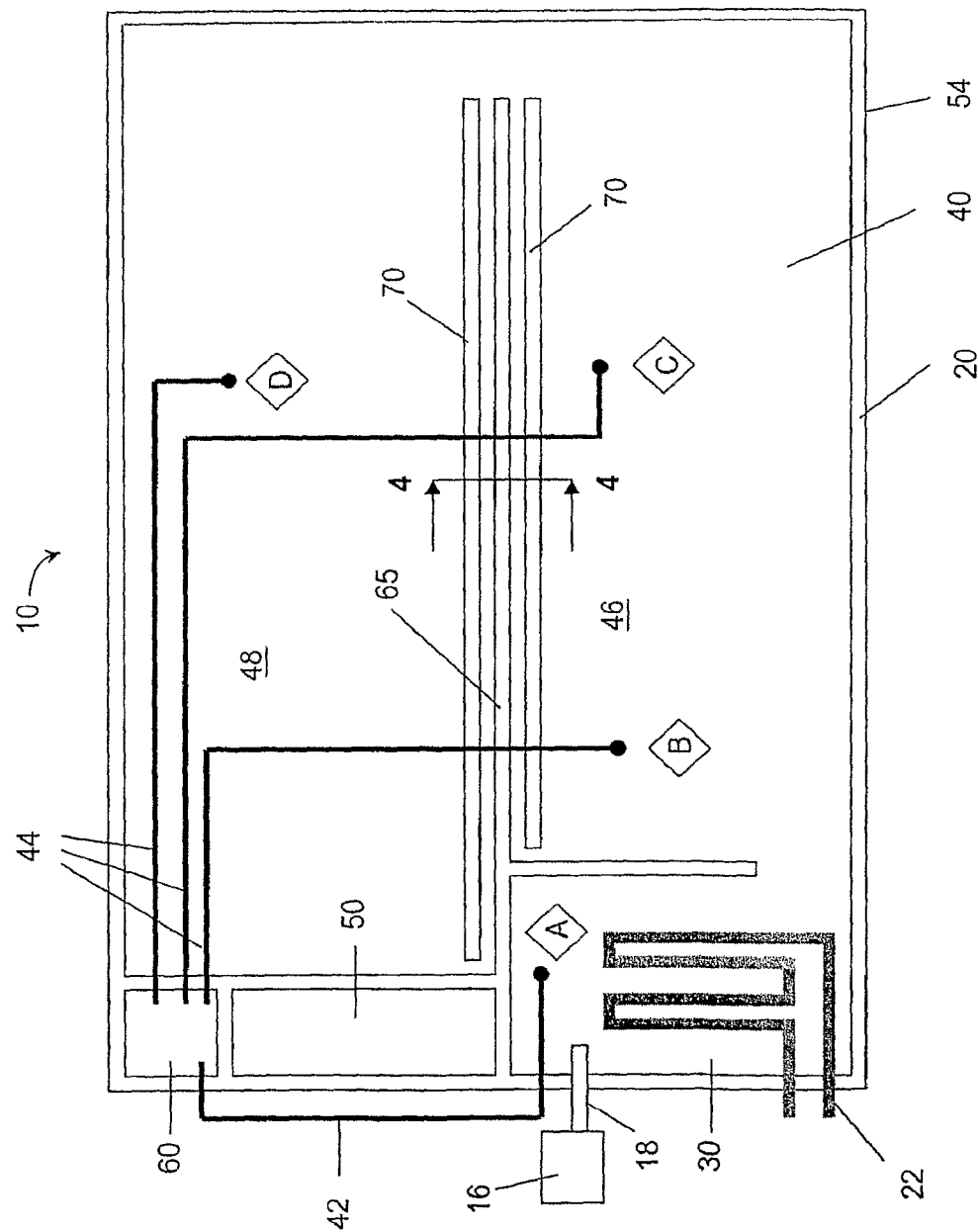
FIG. 1 is a schematic view of a waste treatment system according to one embodiment of the invention.

The present invention relates to the waste treatment of organic liquid waste streams, and more particularly, to the waste treatment of acidic, neutral or alkaline high-strength organic liquid waste streams.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," and "supported" and variations thereof are used broadly and encompass both direct and indirect mountings, connections and supports. Further, "connected" is not restricted to physical or mechanical connections. The word "conduit" is used broadly to represent a pathway, and is not meant to be restricted to any particular physical or mechanical device.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

Treatment of Acidic High-Strength Organic Liquid Wastes

The present invention allows for the treatment of acidic high-strength organic liquid wastes with little or no chemical pH adjustment and without the requirement of blending with other higher pH liquid wastes. This waste treatment system allows the host waste production facility to treat its own wastes economically, on-site with a small plant footprint, and to utilize the resultant high-energy biogas internally in its plant process. As used herein, the term "acidic high-strength organic liquid waste" (hereinafter "acidic liquid waste") means a process waste, organic in nature, with a pH of less than about 5.0 and with a solids content of greater than about 5%.

The challenge in completing the anaerobic degradation of acidic liquid wastes is an imbalance in the biological system. Anaerobic degradation relies on acid forming bacteria to break down the complex carbon molecular structures of the organic input feed into simpler molecular structures such as acetic acid. Subsequently, methanogenic bacteria break down the simpler acid molecular structures into a biogas consisting primarily of methane and carbon dioxide. Suitable acid forming bacteria and methanogenic bacteria may be found in nature, such as, but not limited to, the bacteria found naturally in a cows stomach. Examples of acid forming bacteria may include, but are not limited to, at least one of *Clostridia*, *Fibrobacter succinogenes*, *Ruminococcus albus*, *Butyrivibrio fibrisolvens*, *Selenomonas ruminatium*, *Streptococcuslovis*, *Eubacterium ruminatium*, external enzymes, and combinations thereof. Examples of methanogenic bacteria may include, but are not limited to, at least one of *Methanothrix*, *Methanosarcina*, *Methanospirillum*, *Methanobacterium*, *Methanococcus*, *Methanobrevibacter*, *Methanomicrobiummobile*, *Methanosaeta*, *Methanobacterium thermoautotrophicum*, *Methanobacterium formicicum*, *Methanobacterium thermoalcaliphilum*, *Methanococcus thermolithotrophicus*, *Methanosarcina thermophila*, *Methanosaela thermoacetophila* and combinations thereof. The bacteria production of biogas consumes the acids in the liquid waste and creates a higher pH, alkaline solution. In traditional waste such as municipal and animal wastes, the input wastes have a neutral pH of about 7 and possess sufficient natural fiber and alkalinity so that the acid forming and the acid reducing reactions take place concurrently and the pH of the treatment process remains in the range of about 6.0 to about 8.0. This chemically and biologically balanced system allows for unimpeded degradation of the organic wastes and production of energy in the form of biogas.

Acidic liquid wastes create a special problem for the traditional anaerobic digestion processes. Acid forming bacteria are much more robust, faster population multipliers, and more tolerant of lower pH conditions than the slower breeding, pH sensitive methanogenic bacteria. When presented with an acidic liquid waste that has very slight natural alkalinity with it, such as ethanol by-product wastes, the acid forming bacteria out-produce the methanogenic bacteria. As a result, the pH of the liquid waste rapidly drops to a pH of about 4.0 or less. The entire digestion process stops and the organic waste becomes "dead" due to bacteria inaction at this low pH level. In the traditional mixed anaerobic digester industry, the response to this type of acidic waste and the resultant problems has been digester technology avoidance or continuous heavy chemical usage for pH balancing with high technology/monitoring and low biogas production.

One aspect of the present invention is to modify a plug-flow anaerobic digester system to treat acidic liquid wastes using a two-step anaerobic biodegradation process. In the first step, acid forming bacteria are cultivated to break down the complex carbon molecular structures in the liquid waste into simpler acid molecules. In the second step, methanogenic bacteria are cultivated to subsequently break down the simpler acid molecules into biogas. Examples of plug-flow systems that may be modified for this purpose are disclosed in U.S. Pat. No. 6,451,589 issued to Dvorak on Sep. 17, 2002, U.S. Pat. No. 6,613,562 issued to Dvorak on Sep. 2, 2003, U.S. Pat. No. 7,078,229 issued to Dvorak on Jul. 18, 2006, U.S. application Ser. No. 10/694,244 (U.S. Publication No. 2004/0087011) filed on Oct. 27, 2003, and International Patent Application No. PCT/US2006/045414 entitled "Anaerobic Digester Employing Circular Tank," GHD, Inc. filed on Nov. 27, 2006 (MBF Case No. 031154-9005) the contents of each of which are hereby fully incorporated by reference.

FIGS. 1-4 represent various aspects of one embodiment of the present invention. In FIG. 1, the waste treatment system 10 comprises an influent pH monitoring station 16 and a digester enclosure 20. The digester enclosure 20 encompasses an acid forming chamber 30, a methanic chamber 40, a sludge pit 60, and an effluent pit 50. The acid forming chamber 30 containing the acid forming bacteria and the methanic chamber 40 containing the methanogenic bacteria collectively form an anaerobic digester. The digester enclosure 20 is arranged such that a relatively large methanic chamber 40 may be built in a relatively small space.

Figure 2:
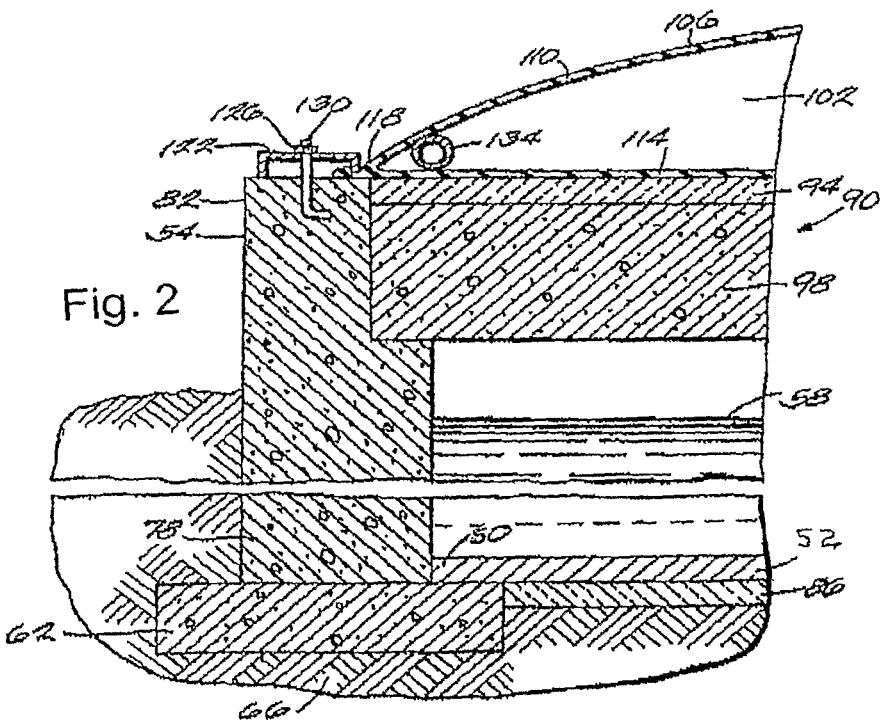
FIG. 2 is a partial cross-section elevational view of the methanic chamber of the waste treatment system shown in FIG. 1.

FIG. 2 illustrates one embodiment of the construction of an outside wall 54 of the digester enclosure 20. The height of the outer wall 54 of the digester enclosure 20 is about 17 feet, with a liquid depth 58 in the digester enclosure 20 of about 14.5 feet. A footing 62 provides an interface between the wall 54 and the ground 66, and supports the wall 54 and the edge 50 of the floor 52. Both the footing 62 and the wall 54 are constructed of poured concrete. The wall 54 is about twelve inches thick at the lower end 78 of the wall 54, and about eight inches thick at the upper end 82 of the wall. The floor 52 of the digester enclosure 20 is about five inches of concrete. Insulation 86 (optional) with a thickness of about four inches is arranged below the floor 52 and provides an interface between the floor 52 and the ground 66.

The roof 90 of the digester enclosure 20 is located about 16 feet above the floor 52 of the digester enclosure 20. The roof 90 is constructed of about ten-inch thickness of hollowcore precast concrete panels 98 (e.g., Spancrete® Hollowcore® available from Spancrete, Inc., Green Bay, Wis.) topped by a layer of insulation 94 with a thickness between about four and about eight inches.

A biogas storage chamber 102 (optional) is located above the roof 90. The primary component of the biogas storage chamber 102 is a liner 106 including an upper liner section 110 and a lower liner section 114. The liner 106 is preferably constructed from high-density polyethylene (HDPE), but may be any other suitable material. The liner 106 is sealed around the edges 118 of the liner 106 by capturing the edges 118 beneath six-inch channel iron 122, which is removably attached to the digester enclosure wall 54 using nuts 126 on a plurality of anchor bolts 130 embedded in the digester enclosure wall 54. A ten-inch PVC pipe 134 is inserted around the periphery of the chamber 102 within the liner 106 to assist in maintaining the seal around the periphery of the liner 106. The liner 106 is constructed such that it can flexibly fill with biogas as the biogas is produced in the methanic chamber 40, and can be emptied of biogas as is needed. The biogas storage chamber 102 may be replaced by any other suitable gas storage system including a roofed storage system.

As shown in FIG. 1, a pH monitoring station 16 measures and adjusts the pH of the influent acidic liquid waste prior to sending the liquid waste to the acid forming chamber 30. The pH of the influent may be monitored by a pH probe that controls a vari-speed chemical feed pump. If the pH of the influent is too low, the chemical pump delivers an alkaline solution that adjusts the initial pH of the influent to a level that facilitates the growth of acid forming bacteria. Examples of such alkaline solutions include solutions of $Ca(OH)_2$, $Mg(OH)_2$, NaOH, KOH, alkaline organic materials, or combinations thereof.

An influent conduit 18 transfers liquid waste from the pH monitoring station to the acid forming chamber 30. An internal heating device 22, such as heat exchanging coils, located within the acid forming chamber 30 maintains the liquid waste at a temperature that facilitates bacterial activity. Stirring mechanisms within the acid forming chamber 30 prevent temperature stratification and promote better bacterial growth. Stirring mechanisms may include, but are not limited to, mechanical stirrers, agitation from recycled biogas, hydraulic agitation with recycled waste liquids, or combinations thereof. A pH monitoring station A in FIG. 1 measures the pH of the liquid waste within the acid forming chamber 30 and triggers the delivery of alkaline sludge from the sludge pit 60 to the acid forming chamber 30 via flow path 42 to maintain the pH of the liquid waste in the acid forming chamber 30 at about 6.0 to about 7.0. Although FIG. 1 shows the alkaline sludge being delivered to the pH monitoring station A in the acid forming chamber 30, it should be understood by one skilled in the art that the alkaline sludge may be delivered to one or more sites located anywhere within the acid forming chamber 30. The flow path 42 may be defined by any number of devices that may include, but are not limited to, a pipe, tile, a channel, and a tube. In some embodiments, the pH monitoring station A triggers a vari-speed sludge recirculation pump. The pump recycles an appropriate amount of alkaline sludge from the sludge pit 60 at the end of the waste treatment system 10 to the liquid waste in the acid forming chamber 30.

Figure 4:
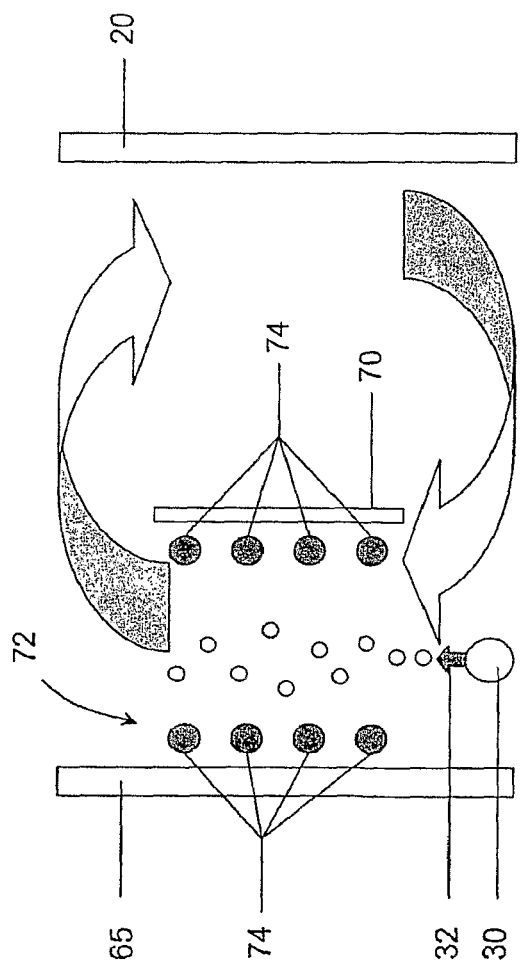
FIG. 4 is a partial cross-sectional view of the methanic chamber taken along the 4-4 line in FIG. 1.

The liquid waste from the acid forming chamber 30 is transferred via horizontal plug-flow movement of the liquid waste to the methanic chamber 40. As shown in FIG. 1, the methanic chamber 40 may be a U-shaped tank with overall horizontal dimensions of about 120 feet long and about 72 feet wide, depending on the volume of liquid wastes to be treated. A center wall 65 divides the methanic chamber 40 into a first leg or passageway 46 and second leg or passageway 48 of the U-shape. One or more partitions 70 may run severally parallel to, and on opposite sides of, the center wall 65. The partitions 70 may comprise at least one of a rigid board or plank, curtain or drape, tarp, film, and a combination thereof. In addition, the partitions 70 may be constructed of a variety of materials including, without limitation, at least one of a metal, wood, polymer, ceramic, composite, and a combination thereof. As illustrated in FIG. 4, the partitions 70 are shorter than the center wall 65 and are raised off the floor of the methanic chamber 40. This allows liquid waste to flow underneath and then over the partitions 70 as it plug flows through the methanic chamber 40. In some embodiments, the center wall 65 rises about 16 feet off the floor of the methanic chamber 40. The partitions 70 are about 10 feet 6 inches high and sit about 2 feet above the floor of the methanic chamber 40. The partitions 70 are about 2 feet away from the center wall 65. The digester enclosure 20 is about 36 feet from the center wall 65.

Figure 3:
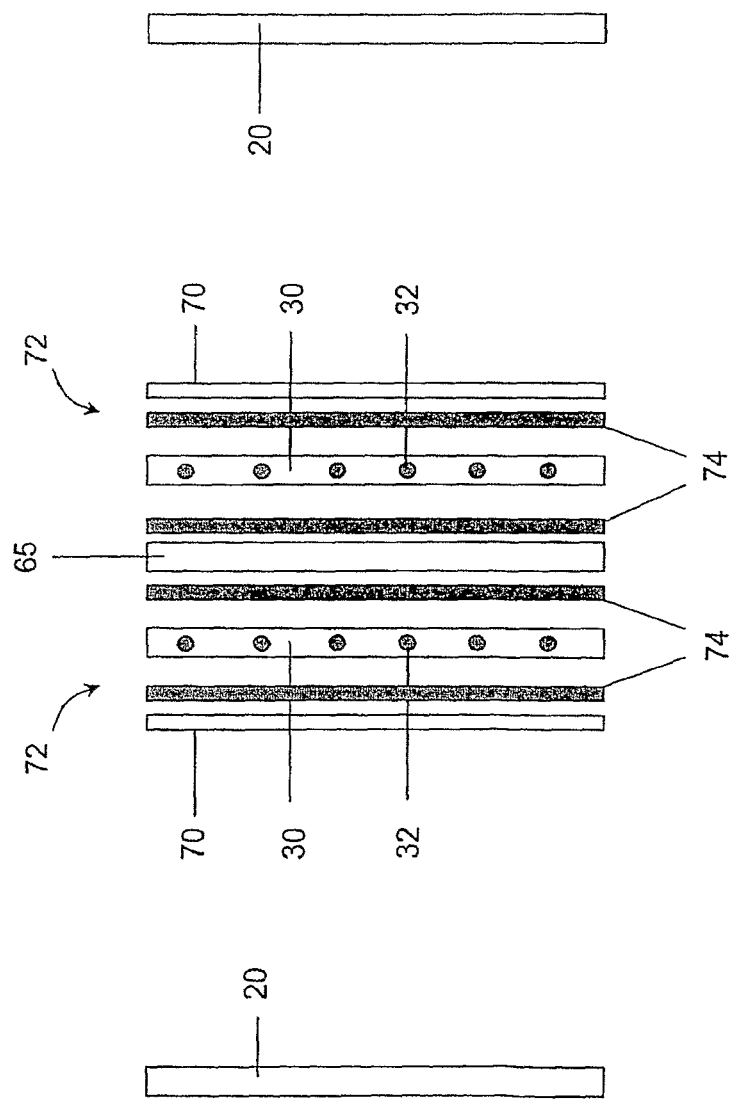
FIG. 3 is a partial top plan view of the methanic chamber shown in FIG. 1.

As shown in FIGS. 3-4, an internal heating device 72 is located within the methanic chamber 40 to maintain the liquid waste at a temperature that facilitates bacterial activity. The heating device 72 may be used for heating or cooling as determined by the influent liquid temperature. In the embodiment shown in FIGS. 3-4, the heating device 72 comprises a series of heating conduits 74 that run parallel to the center wall 65. The heating conduits 74 each contain a heating medium. Any variety of heating media may be used including, but not limited to, water and gas. The heating conduits 74 are arranged in a two-by-four grid. However, it should be recognized by those skilled in the art that any number of heating conduits 74 may be arranged in a variety of configurations without departing from the spirit and scope of the present invention. Moreover, other heating devices known to those skilled in the art may be employed including, but not limited to, heating coils.

In addition to controlling the temperature within the methanic chamber 40, the heating device 72 may facilitate the mixing of the liquid waste as it flows through the methanic chamber 40. The heating device 72 may be used to heat the liquid waste, causing the heated liquid waste to rise up the center wall 65 under convective forces. In embodiments employing one or more partitions 70, heated waste material flows upwardly in the space created between the partitions 70 and the center wall 65. At the same time, liquid waste near the inner wall of the relatively cooler digester enclosure 20 falls under convective forces. As a result, the convective forces cause the liquid waste to follow a circular flow path upward along the center wall 65 and downward along the digester enclosure 20. At the same time, the liquid waste flows along the first leg 46 and second leg 48 of the methanic chamber 40, resulting in a combined corkscrew-like flow path for the liquid waste. Mixing of the plug flow prevents stratification in the digester.

Stirring mechanisms are also located within the methanic chamber 40 and may include mechanical stirrers, agitation from recycled biogas, hydraulic agitation with recycled liquid waste, or combinations thereof. In some embodiments, recycled biogas agitation is maintained for waste mixing in a direction perpendicular to the waste flow direction. As illustrated in FIGS. 3 and 4, one or more gas conduits 30 may run parallel to, and in-between, the center wall 65 and the partitions 70. Air diffuser nozzles 32 located along the gas conduits 30 dispense biogas upward and parallel to the center wall 65. As liquid waste plug flows through the methanic chamber 40, liquid waste is drawn underneath the partitions 70 by the vertical rising of the gas and forced back over the top of the partitions 70, creating a similar corkscrew-like flow path through the methanic chamber 40. The air diffuser nozzles can be a variety of sizes, including ¾ inch.

pH monitoring stations are located at various sites throughout the methanic chamber 40 to maintain the pH of the liquid waste at a level that facilitates bacterial activity. FIG. 1 shows three such pH monitoring stations (B-D). However, any number of pH monitoring stations can be distributed throughout the methanic chamber 40. The number of such stations may depend upon such factors as the nature of the liquid waste, activity of the methanogenic bacteria, and system flow rates. When the pH of the liquid waste drops below an acceptable level, pH monitors trigger the delivery of alkaline sludge via one or more flow paths 44 from the sludge pit 60 to the methanic chamber 40. In some embodiments, the pH monitors trigger a vari-speed sludge recirculation pump that delivers an appropriate amount of alkaline sludge to the methanic chamber 40. Although FIG. 1 shows the alkaline sludge being delivered to the pH monitoring stations (B-D) in the methanic chamber 40, it should be understood by one skilled in the art that the alkaline sludge may be delivered to one or more sites located anywhere within the methanic chamber 40. The flow paths 44 may be defined by any number of devices that may include, but are not limited to, a pipe, tile, a channel, and a tube.

In addition to producing activated sludge, the anaerobic digestion in the methanic chamber 40 also produces biogas in the form of methane gas, which is collected above the liquid level 58 and can be stored in the biogas storage chamber 102, or utilized directly as a bio-fuel. Liquid that condenses within the chamber 102 may be directed through an effluent conduit to a liquid storage lagoon. The collected biogas may be used to fuel an internal combustion engine that, in combination with an electric generator, may be used to produce electricity that is used within the waste treatment system 10, sold to a power utility, or a combination thereof. The cooling system of the internal combustion engine may also produce hot coolant that may be used to heat liquid waste in the acid forming chamber 30 and/or to heat and agitate the liquid waste in the methanic chamber 40. Hot water from the engine may pass through an air/water cooler to reduce the temperature of the water from the about 180° F. temperature at the exit of the engine to about 160° F. for use in the acid forming chamber 30 and the methanic chamber 40.

The effluent pit 50 is located adjacent to the sludge pit 60. The liquid waste plug flows sequentially from the acid forming chamber 30 into the methanic chamber 40 into the sludge pit 60 and into the effluent chamber 50. At least a portion of the sludge may be recirculated via one or more flow paths 42, 44 to the acid forming chamber 30 and methanic chamber 40. In some embodiments, a sump conduit from the effluent chamber 50 leads to a standard solids press to separate the digested liquid from the digested solids. The liquid from the solids press may be recycled to the acid forming chamber 30 for further processing. The solids from the solid press may be sent to a composter and bagged for commercial sale.

A natural gravity system may be used to separate solids from liquids in the sludge pit 60 at the end of the waste treatment system 10. However, it should be understood by one skilled in the art that any solid-liquid separator may be used in place of, or in addition to, the gravity system. Any solid-liquid separator that separates solids from liquids by gravity, differential settling velocity, or size-exclusion may be employed. Examples of additional solid-liquid separators include settling ponds, hydrocyclones, centrifuges, and membrane filters or separators.

In operation of the waste treatment system 10, as illustrated in FIG. 1, acidic liquid waste is transported to the waste treatment site. Prior to entering the acid forming chamber 30, the pH of the liquid waste influent is measured and, if necessary, the pH of the influent is adjusted to a range of between about 6.0 and about 7.0 to start the acid forming bacterial growth. In one embodiment, a pH probe that controls a vari-speed chemical feed pump is utilized to monitor and adjust the initial pH of the influent. Agents used to adjust the pH may include a variety of alkaline substances, such as solutions of $Ca(OH)_2$, $Mg(OH)_2$, NaOH, KOH, alkaline organic materials, or combinations thereof.

The liquid waste is transferred from the pH monitoring station 16 via the influent conduit 18 to the acid forming chamber 30. In the acid forming chamber 30, the internal heating device 22 adjusts the temperature of the influent to facilitate the growth of acid forming bacteria. Temperature control is important for methanogenic bacteria (less so for acid forming bacteria) and the temperature is closely regulated in the acid forming chamber 30 so that the temperature is kept constant as the liquid "plug flows" from the acid forming chamber 30 into the methanic chamber 40. The temperature can be site determined to be about 97° F. to about 103° F. for a mesophilic operating digester or about 132° F. to about 138° F. for a thermophilic digester. The liquid waste in the acid forming chamber 30 is continuously stirred to eliminate temperature stratification in the liquid waste and to promote better bacterial growth. In one embodiment, the contents of the acid forming chamber are continuously stirred with recycled biogas agitation.

Within the acid forming chamber 30, acid forming bacteria convert complex carbon molecules into simpler acids. These acids in turn lower the pH of the liquid waste in the acid forming chamber 30. In order to prevent the pH from dropping too low to sustain bacterial activity, the pH of the liquid waste must be frequently adjusted upward. Rather than add additional pH adjusters from outside the waste treatment system, the pH can be adjusted internally by mixing alkaline sludge from the sludge pit 60 at the end of the waste treatment system 10 with the existing influent in the acid forming chamber 30 to maintain the pH of the influent at about 6.0 to about 7.0 for maximum acid-forming bacteria growth rates and efficiency. The pH of the sludge in the sludge pit is typically between about 7.0 to about 8.0. In addition to changing pH, the sludge can also "seed" the influent in the acid forming chamber 30 with mature acid forming bacteria and methanogenic bacteria. In some embodiments, a roof mounted pH monitor identified by station A in FIG. 1 controls a vari-speed sludge recirculation pump to recycle sludge from the sludge pit 60 at the end of the waste treatment system 10 to the influent in the acid forming chamber 30. The flow rate of recycled sludge is determined by the need for pH blending, which is ultimately determined by the growth rate of the acid forming bacteria.

As new influent enters the acid forming chamber 30, the treated liquid waste within the acid forming chamber 30 will plug flow into the methanic chamber 40. In the methanic chamber 40, an environment to foster the growth of the methanogenic bacteria is maintained. The pH of the liquid waste in the methanic chamber 40 is maintained at a pH of about 6.5 to about 8.0, and particularly at a pH of about 7.5 to about 8.0. To accomplish this, pH monitoring stations (B-D) are located throughout the methanic chamber 40. If the drops below a set value, such as 6.5, at any of these stations, the pH monitors will activate one or more vari-speed sludge recirculation pumps to add alkaline sludge from the sludge pit 60 to the liquid waste in the methanic chamber 40. The corkscrew mixing of the liquid waste in the methanic chamber 40 by the utilization of the recirculated biogas and/or heating ensures a homogeneous pH mix and prevents pH stratification within the vessel. Heat exchanging coils within the methanic chamber 40 maintain the temperature of the liquid waste within a range of about 1 to about 2 degrees of the set point temperature. The set point temperature for a mesophilic temperature digester will be about 100° F. and about 134° F. for a thermophilic digester. The heating coils can be utilized for heating or cooling as determined by the influent liquid temperature. The liquid waste within the methanic chamber 40 is continuously mixed with recycled biogas jetted into the liquid waste in a direction perpendicular to the waste flow direction. Mixing prevents stratification within the methanic chamber and enhances biodegradation.

As the waste stream plug flows through the methanic chamber 40, it is not mixed with the newer incoming waste material and is, therefore, allowed to biodegrade in multiple sections as it travels in a horizontal corkscrew-like pathway through the first leg 46 and the second leg 48 of the methanic chamber 40. As the methanogenic bacteria function, they consume the acids created in the acid forming chamber 30 and effectively raise the pH of the liquid waste stream and increase the alkalinity of the liquid waste. At the end of the methanic chamber 40, with properly engineered hydraulic retention times based on influent characteristics, the acid forming bacteria will have long completed their function and the methanogenic bacteria will have consumed the bacteria-produced acids. This results in a waste effluent of high pH and alkalinity in comparison to the influent. The greatest alkalinity and bacteria population at the very end of the waste treatment system 10 will be in the bacteria "sludge" that is allowed to settle in the sludge pit 60 located at the end of the waste treatment system 10. The sludge pit 60 does not have mixing and thus the sludge is allowed to settle to the bottom. This sludge, with its higher alkalinity, pH, and bacteria population, is the recirculated sludge utilized at the various points (stations A, B, C and D) throughout the waste treatment system 10 for pH control and bacterial seeding.

The biodegraded effluent may be further treated or disposed of by the generating facility as required. Biogas generated by the anaerobic biological process may be collected in the gas collection space above the liquid level and under the ceiling of the methanic chamber 40. The biogas may be utilized as a "BTU replacement" in the production of electricity or natural gas.

The waste treatment system 10 will treat acidic liquid wastes with a solids percentage varying between about 5% and about 40%. It does this by monitoring and closely controlling the pH in the liquid waste and by utilizing the naturally generated alkalinity and pH rise associated with the two-step anaerobic biodegradation process of acid forming bacteria followed by methanogenic bacteria and their resultant biological waste products. Use of a mixed plug flow is preferred. Additionally, the plug-flow separation of the processed wastes over the designed hydraulic retention time enables the natural increase in pH and alkalinity, thus allowing for the production of the returned sludge. Mixing of the plug flow prevents stratification in the acid forming chamber 30 and methanic chamber 40. Eliminating stratification in the acid forming chamber 30 and methanic chamber 40 prevents buildup of acid forming bacteria colonies and the resultant high acidic liquid (low pH) "dead" spots, facilitates better methanogenic bacteria growth to achieve better and faster acid neutralization and alkalinity production, and provides for more uniform hydraulic retention time in the waste treatment system 10 by preventing "short circuiting" of the liquid pathflow.

Figure 5:
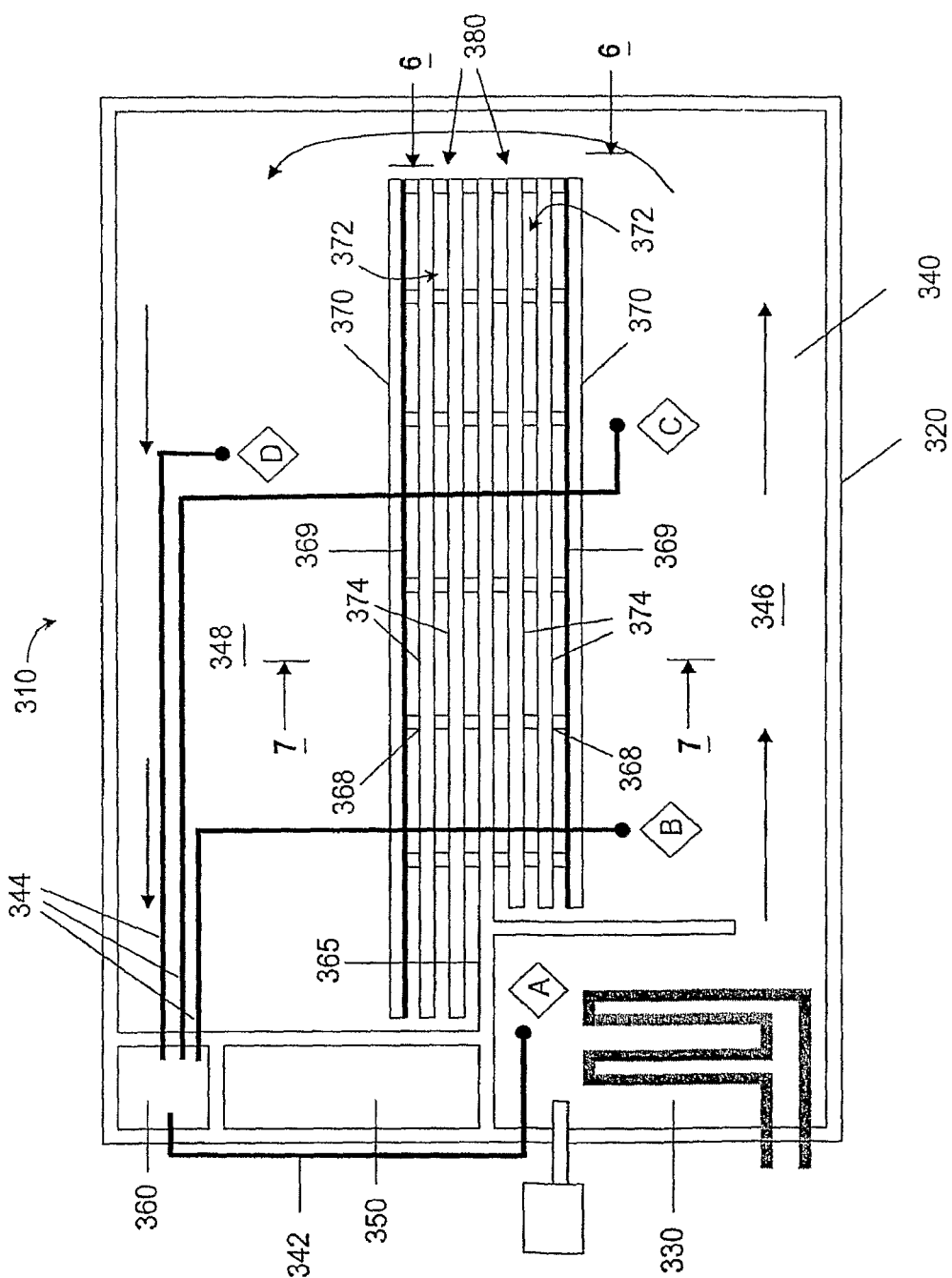
FIG. 5 is a schematic view of an alternative waste treatment system according to another embodiment of the invention.
Figure 6:
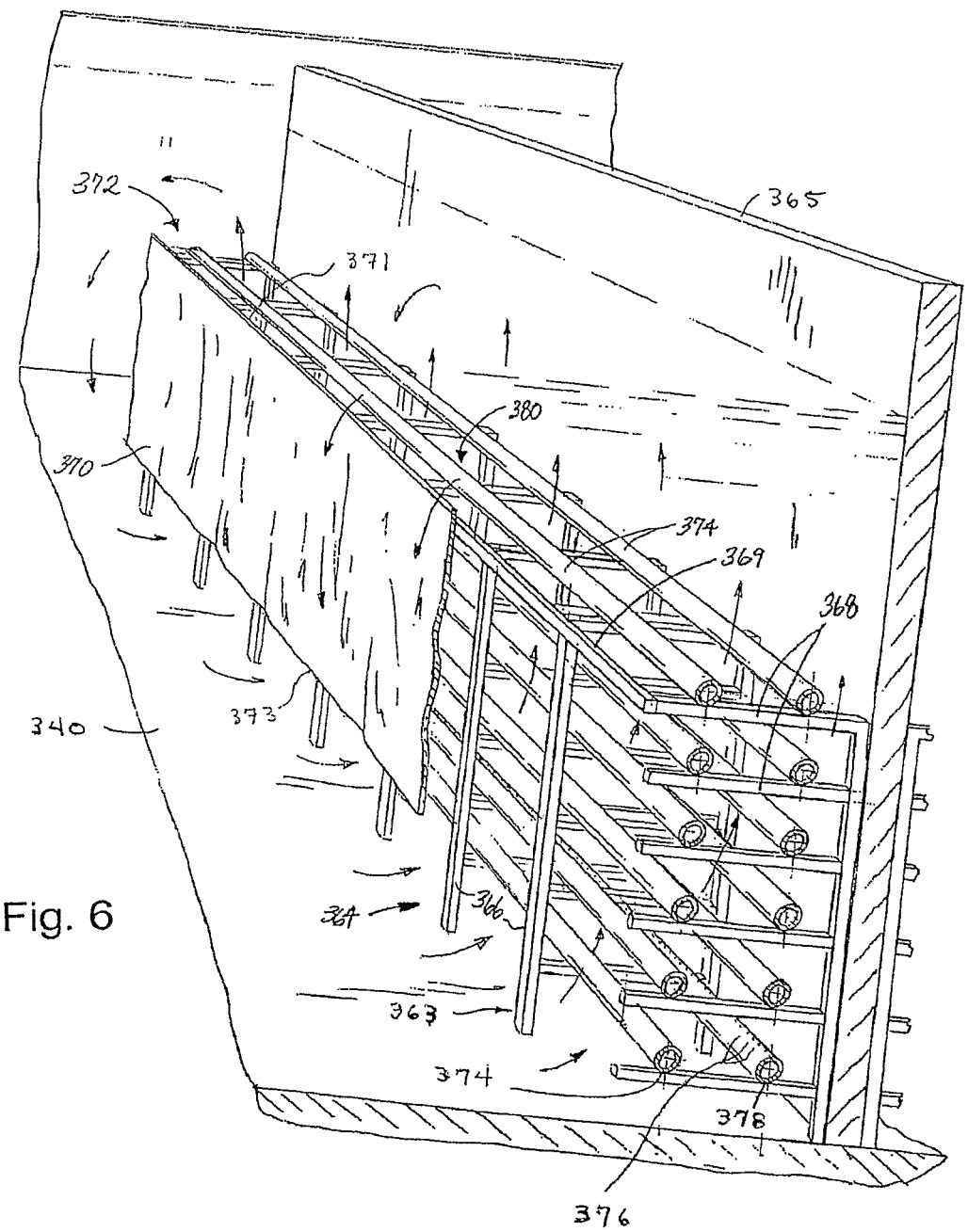
FIG. 6 is a partial cross-sectional view of a methanic chamber taken along the 6-6 line in FIG. 5.
Figure 7:
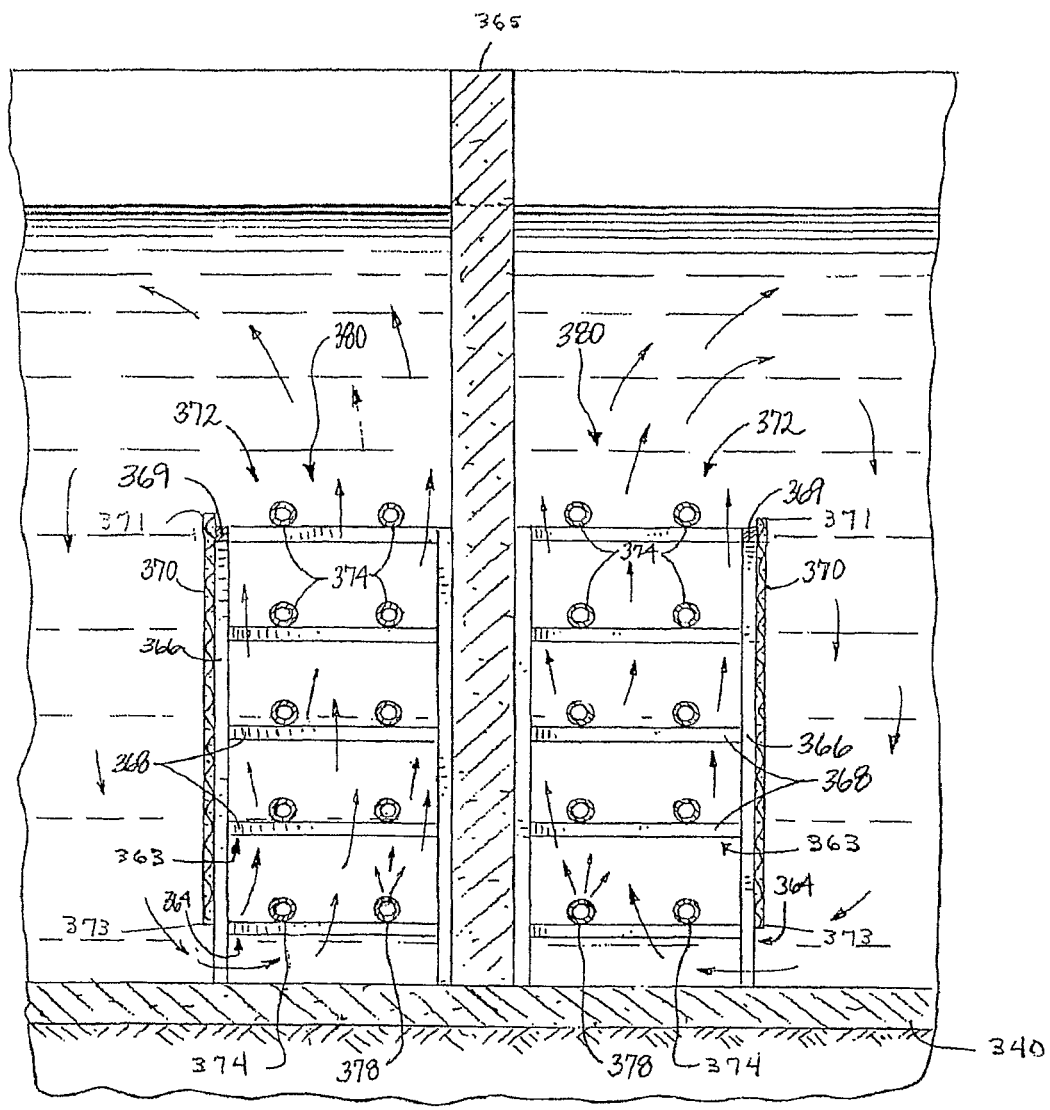
FIG. 7 is a partial cross-section elevational view of the digester taken along the 7-7 line in FIG. 5.

FIGS. 5-7 illustrate an alternate embodiment of a waste treatment system according to the present invention. The waste treatment system 310 shown in FIGS. 5-7 is similar in many ways to the illustrated embodiments of FIGS. 1-4 described above. Accordingly, with the exception of mutually inconsistent features and elements between the embodiment of FIGS. 5-7 and the embodiment of FIGS. 1-4, reference is hereby made to the description above accompanying the embodiment of FIGS. 1-4 for a more complete description of the features and elements (and the alternatives to the features and elements) of the embodiment of FIGS. 5-7. Features and elements in the embodiment of FIGS. 5-7 corresponding to features and elements in the embodiment of FIGS. 1-4 are numbered in the 300 series.

As shown in FIG. 5, the waste treatment system 310 includes a digester enclosure 320, an acid forming chamber 330, a methanic chamber 340, a sludge pit 360 and an effluent pit 350. pH monitoring stations A-D adjust the pH of the liquid waste in the acid forming chamber 330 and methanic chamber 340 by recycling alkaline sludge from the sludge pit 360 via one or more flow paths 342, 344. The system 310, or portions of the system 310, may be anaerobic. A center wall 365 divides the methanic chamber 340 into a first leg or passageway 346 and a second leg or passageway 348. The liquid waste can therefore move from the acid forming chamber 330 into the methanic chamber 340 along the first leg 346 in a first direction, and toward the sludge pit 360 along the second leg 348 of the methanic chamber 340 in a second direction opposite the first direction.

The first leg 346 and the second leg 348, as illustrated in FIG. 5, each include a partition 370 positioned relative to the center wall 365 such that a space 380 is created between the partitions 370 and the center wall 365. The partitions 370 may comprise at least one of a rigid board or plank, curtain or drape, tarp, film, and a combination thereof. In addition, the partitions 370 may be constructed of a variety of materials including, without limitation, at least one of metal, wood, polymer, ceramic, composite, and a combination thereof. The first leg 346 and the second leg 348 each further include a heating device 372 positioned within the space 380 between the partitions 370 and the center wall 365 such that liquid waste is heated as it contacts the heating device 372. Heated liquid waste rises relative to cooler liquid waste by free convection and is allowed to rise upwardly within the space 380.

The heating device(s) 372 and the partition(s) 370 are shown in greater detail in FIGS. 6 and 7. For simplicity, one of the heating devices 372 and one of the partitions 370 will be described in greater detail, but it should be noted that the description may equally apply to the other heating device 372 and partition 370. As shown in FIGS. 6 and 7, the heating device 372 includes a series of conduits 374, each containing a heating medium. A variety of heating media may be used with the present invention, including at least one of water and a gas. The conduits 374 do not all need to contain the same heating medium. That is, some of the conduits 374 may contain a gas, while others contain a liquid, such as water.

As illustrated in FIGS. 6 and 7, the waste treatment system 310 may further include at least one conduit 378, which contains a compressed, recycled biogas from the biogas storage area (not shown) and has nozzles 376. The nozzles 376 are gas outlets. The compressed biogas contained in the conduit 378 flows through the conduit 378 and out the nozzles 376, such that as the gas escapes the conduit 378 via the nozzles 376, the gas is propelled upwardly in the space 380 to promote the liquid waste to move upwardly through the principle of air/water lifting. FIGS. 6 and 7 illustrate one conduit 378 having nozzles 376. Any number of conduits 378 having nozzles 376 can be used without departing from the spirit and scope of the present invention. The nozzles 376 may be simple holes drilled into conduit 378 or may be specialized nozzles attached to conduit 378 via welding or tapping.

Referring to FIGS. 6 and 7, a frame 364 is positioned within the space 380 to support the heating device 372 and conduit 378. The frame 364 is illustrated as comprising a plurality of ladder-like units 363 and a connecting bar 369 running generally parallel to the center wall 365 to connect the units 363. Each unit 363, as illustrated in FIGS. 6 and 7, is formed of two vertical columns 366 positioned on opposite sides of the space 380 and a plurality of crossbeams 368 connecting the two vertical columns 366 across the space 380. The frame 364 is illustrated by way of example only, and the present invention is in no way limited to the illustrated support structure. A variety of frame elements can be used to support the heating device 372, conduit 378, and/or other components of the waste treatment system 310 within the space 380 without departing from the spirit and scope of the present invention.

As illustrated in FIGS. 6 and 7, the partition 370 has a top edge 371 and a bottom edge 373. In addition, the illustrated partition 370 is substantially vertical and shorter in height than the methanic chamber 340, such that heated liquid waste can move over the top edge 371 of the partition 370 and out of the space 380 between the partition 370 and the center wall 365, and cooled liquid waste can move under the bottom edge 373 of the partition 370 and into the space 380. Therefore, as illustrated by the arrows in FIGS. 6 and 7, the partition 370, in conjunction with the heating device 372, promotes upward and downward movement of the liquid waste. This upward and downward movement of the liquid waste results in an overall corkscrew-like movement of the liquid waste as the liquid waste is moved along the first and second legs 346, 348 of the methanic chamber 340. Further promoting this corkscrew-like flowpath is conduit 378 with nozzles 376, which is located beneath the series of conduits 374 of the heating device 372 closest to the center wall 365 in FIGS. 6 and 7. The corkscrew-like flowpath of the liquid waste throughout the methanic chamber 340 promotes thermal mixing of the liquid waste.

The series of conduits 374, 378 illustrated in FIG. 6 is formed by having a two-by-six configuration within the space 380 (i.e. two conduits 374, 378 across and five conduits 374, 378 up and down), with the conduits 374, 378 running generally parallel to the center wall 365. Another example is a two-by-five configuration, as shown in FIG. 7. As illustrated in FIGS. 6 and 7, one of the conduits 378 having nozzles 376 transports compressed biogas and the remaining conduits 374 transport heating media. It should be noted, however, that any number of conduits 374 containing heating media and any number of conduits 378 having nozzles 376 can be combined in a variety of configurations without departing from the spirit and scope of the present invention. The series of conduits 374 and the conduit 378 having nozzles 376 depicted in FIGS. 5-7 are shown by way of example only.

Figure 8:
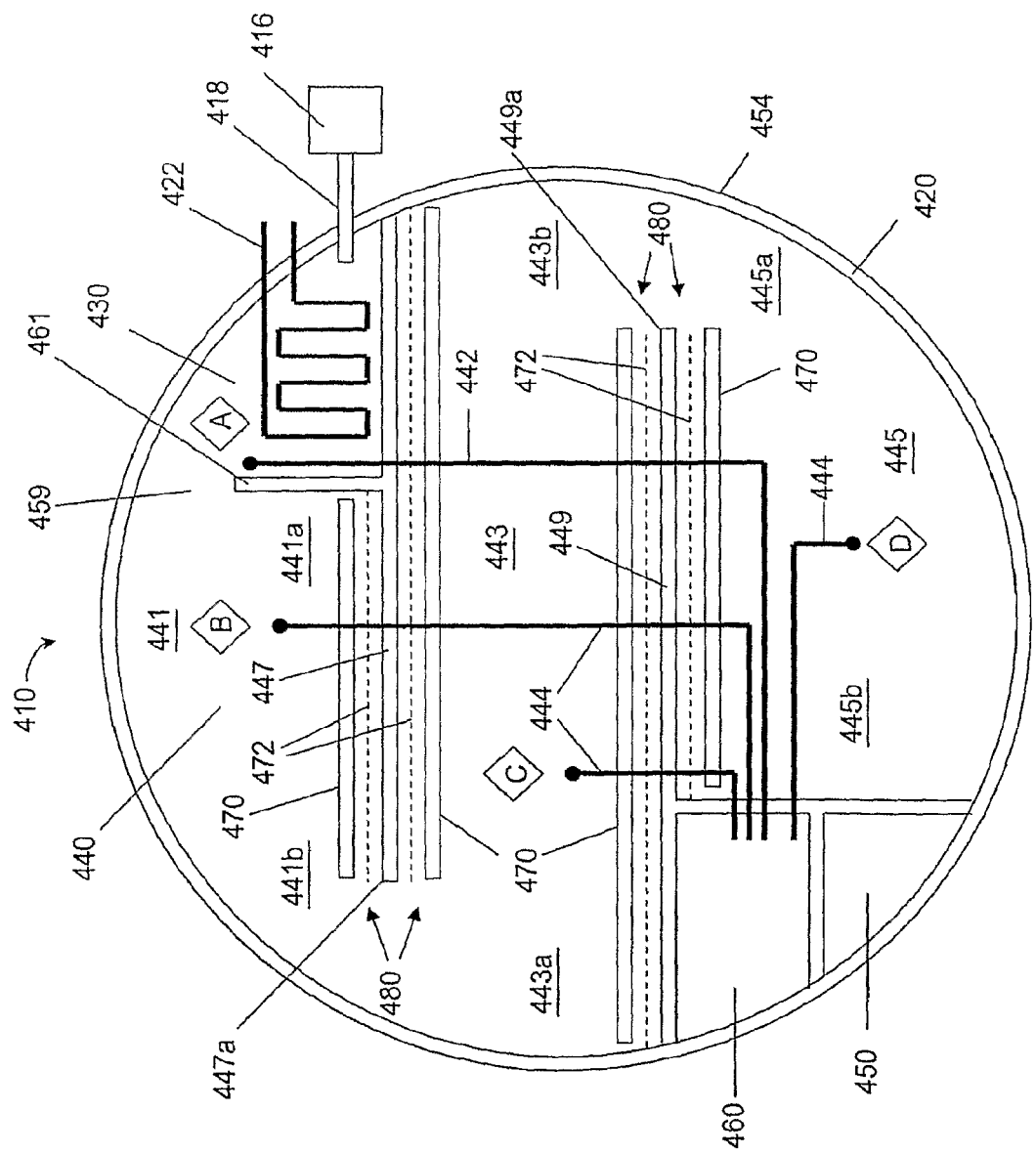
FIG. 8 is a schematic view of a waste treatment system according to yet another embodiment of the invention.

FIG. 8 illustrates an alternate embodiment of a waste treatment system according to the present invention. The waste treatment system 410 shown in FIG. 8 is similar in many ways to the illustrated embodiments of FIGS. 1-7 described above. Accordingly, with the exception of mutually inconsistent features and elements between the embodiment of FIG. 8 and the embodiments of FIGS. 1-7, reference is hereby made to the description above accompanying the embodiments of FIGS. 1-7 for a more complete description of the features and elements (and the alternatives to the features and elements) of the embodiment of FIG. 8. Features and elements in the embodiment of FIG. 8 corresponding to features and elements in the embodiments of FIGS. 1-7 are numbered in the 400 series.

FIG. 8 illustrates a waste treatment system 410 which includes a pH monitoring station 416, a digester enclosure 420, an acid forming chamber 430, a methanic chamber 440, a sludge pit 460 and an effluent pit 450. The system 410, or portions of the system 410, may be anaerobic. The digester enclosure 420 is arranged such that a relatively large methanic chamber 440 may be built in a relatively small space.

As illustrated in FIG. 8, an outer wall 454 of the digester enclosure 420 is generally circular, such that an outer perimeter of the digester enclosure 420 is generally circular as well. Furthermore, the outer wall 454 forms at least a portion of the outer perimeter of the acid forming chamber 430, methanic chamber 440, sludge pit 460 and effluent pit 450. In other words, each of the acid forming chamber 430, methanic chamber 440, sludge pit 460 and effluent pit 450 has an outer perimeter defined by the generally circular outer wall 454 of the digester enclosure 420.

The acid forming chamber 430 includes an influent conduit 418 for receiving liquid waste from the pH monitoring station 416 into the acid forming chamber 430. A cutout 459 is formed in a wall 461 between the acid forming chamber 430 and the methanic chamber 440 to allow liquid waste to flow from the acid forming chamber 430 into the methanic chamber 440. The acid forming chamber 430 also includes a heating device 422 for heating the liquid waste as it flows through the acid forming chamber 430. The heating device 422 may, for example, be a heating conduit or other conduit containing a liquid or gas. The heating device 422 may include discharge nozzles (not shown) to further agitate the liquid waste. Additionally, a pH monitoring station A measures the pH of the liquid waste within the acid forming chamber 430 and triggers the delivery of alkaline sludge from the sludge pit 460 to the acid forming chamber 430 via flow path 442 to maintain the pH of the liquid waste in the acid forming chamber 430 at about 6.0 to about 7.0.

The methanic chamber 440 includes a first leg or passageway 441, a second leg or passageway 443 and a third leg or passageway 445. The first and second legs 441, 443 are separated from one another by a first divider 447, while the second and third legs 443, 445 are separated from one another by a second divider 449. The first leg 441 has a first end 441a and a second end 441b, the second leg 443 has a first end 443a and a second end 443b, and the third leg 445 has a first end 445a and a second end 445b. The first end 441a of the first leg 441 is adjacent the cutout 459, which thus also serves as an inlet for receiving liquid waste into the methanic chamber 440. The second end 441b of the first leg 441 is adjacent the first end 443a of the second leg 443. The second end 443b of the second leg 443 is adjacent the first end 445a of the third leg 445. The second end 445b of the third leg 445 is adjacent the sludge pit 460. The first divider 447 has an end 447a around which the liquid waste flows from the first leg 441 to the second leg 443. Likewise, the second divider 449 has an end 449a around which the liquid waste flows from the second leg 443 to the third leg 445. From the methanic chamber 440, the liquid waste flows into the optional sludge pit 460.

The methanic chamber 440 forms a flow path for the liquid waste that is generally S-shaped. It should be noted, however, that additional dividers could be employed to increase the length of the flow path, by adding additional legs or passageways. The methanic chamber 440 provides a relatively long flow path for the liquid waste within the relatively small area enclosed by the outer wall 454.

The methanic chamber 440 may optionally include one or more partitions 470 positioned relative to the first divider 447 and the second divider 449 such that a space 480 is created between the partition 470 and the respective divider. The partitions 470 may comprise at least one of a rigid board or plank, curtain or drape, tarp, film, and a combination thereof. In addition, the partition 470 may be constructed of a variety of materials including, without limitation, at least one of metal, wood, polymer, ceramic, composite, and a combination thereof. The illustrated partition 470 is substantially vertical and shorter in height than the methanic chamber 440, such that heated liquid waste can move over the top edge of the partition 470 and out of the space 480 between the partition 470 and the divider 447, and cooled liquid waste can move under the bottom edge of the partition 470 and into the space 480.

The waste treatment system 410 as illustrated in FIG. 8 may include any of the features discussed with respect to the previous embodiments. For example, the methanic chamber 440 may include a heating device 472 for heating the liquid waste as it flows through the methanic chamber 440. In one embodiment, the heating device 472 includes one or more heating conduits (not shown) arranged along one or both of the dividers 447, 449 within the first leg 441, the second leg 443, the third leg 445, or a combination thereof. The heating conduits locally heat the liquid waste using, for example, hot water or gas, causing the heated mixed liquid waste to rise under convective forces. The convective forces cause the heated liquid waste to rise near the first and second dividers 447, 449. At the same time, liquid waste near the relatively cooler outer wall 454 falls under convective forces. As a result, the convective forces cause the liquid waste to follow a circular flow path through the first leg 441 upward along the divider 447 and downward along the outer wall 454. Likewise, the convective forces cause the liquid waste to follow a circular flow path through the third leg 445 upward along the second divider 449 and downward along the outer wall 454. At the same time, the liquid waste flows along the first, second and third legs 441, 443, 445, resulting in a combined corkscrew-like flow path for the liquid waste. The heating conduits may include jet nozzles to dispense water or gas into the liquid waste. In another embodiment, hot gas injection jets using heated gases from the output of the engine (not shown) replace the hot water heating conduits as a heating and current-generating source. The injection of hot gases circulates the liquid waste through both natural and forced convection. A similar corkscrew-like flow path is thereby developed in the methanic chamber 440. In a further embodiment, at least one conduit containing compressed, recycled biogas is used in combination with the heating device 472. The compressed biogas contained in the conduit is forced out of the conduit and propelled upwardly to promote the liquid waste to move upwardly through the principle of air/water lifting. The released gas may also facilitate the corkscrew-like flow path of liquid waste through the methanic chamber 440.

Although the above embodiments were described in the context of treating acidic liquid wastes, it should be understood by those skilled in the art that the same embodiments may also be used to treat high-strength organic liquid wastes having an influent pH of about 7.

Treatment of Alkaline High-Strength Organic Liquid Wastes

Another aspect of the present invention is to modify a plug-flow anaerobic digester system to treat alkaline high-strength organic liquid wastes. As used herein, the term "alkaline high-strength organic liquid waste" (hereinafter "alkaline liquid waste") means a process waste, organic in nature, with a pH greater than about 8.0 and with a solids content greater than about 5%.

Figure 9:
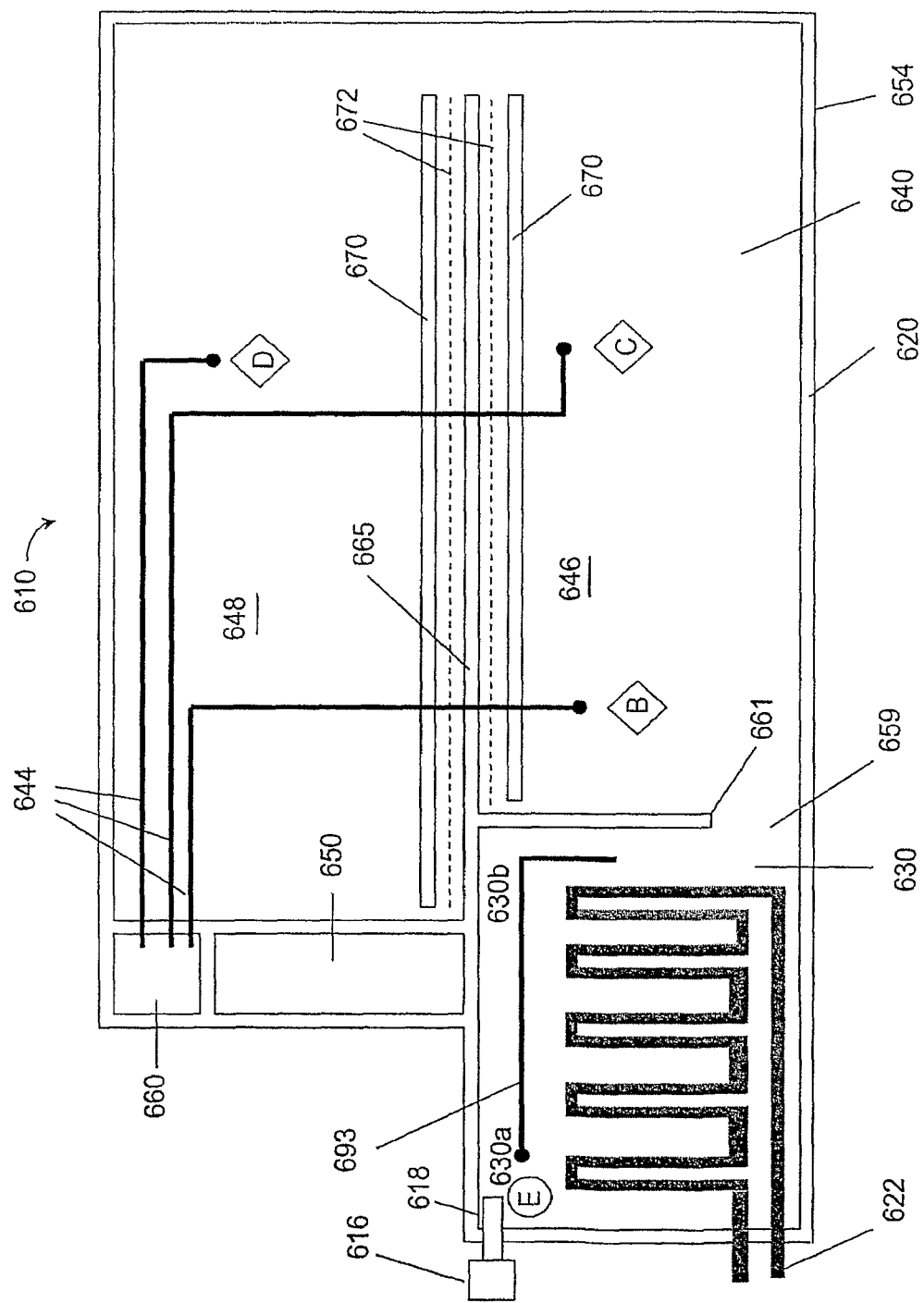
FIG. 9 is a schematic view of a waste treatment system according to another embodiment of the invention.

FIG. 9 illustrates one embodiment of an alkaline waste treatment system according to the present invention. The waste treatment system 610 shown in FIG. 9 is similar in many ways to the acidic waste treatment system illustrated in the embodiment of FIGS. 1-4 described above. With the exception of mutually inconsistent features and elements between the embodiment of FIG. 9 and the embodiment of FIGS. 1-4, reference is hereby made to the description above accompanying the embodiment of FIGS. 1-4 for a more complete description of the features and elements (and the alternatives to the features and elements) of the embodiment of FIG. 9. Features and elements in the embodiment of FIG. 9 corresponding to features and elements in the embodiment of FIGS. 1-4 are numbered in the 600 series.

As shown in FIG. 9, the waste treatment system 610 includes a digester enclosure 620, an acid forming chamber 630, a methanic chamber 640, a sludge pit 660 and an effluent pit 650. The system 610, or portions of the system 610, may be anaerobic. An optional pH monitoring station 616 may be used to adjust the pH of the influent liquid waste prior to sending the liquid waste to the acid forming chamber 630. If the liquid waste is alkaline, the pH of the liquid waste may be adjusted to a pH of about 7.0 with the addition of acidic material. Acidic material may include, but is not limited to, industrial acids (e.g., $H_2SO_4$), acidic liquid animal wastes, or acidic organic liquid wastes.

The acid forming chamber 630 includes an influent conduit 618 for receiving liquid waste from outside the digester enclosure 620 into the acid forming chamber 630. The acid forming chamber 630 has an upstream end 630a and a downstream end 630b. Liquid waste enters the acid forming chamber 630 at the upstream end 630a and exits the acid forming chamber 630 at the downstream end 630b. A cutout 659 is formed in a wall 661 between the acid forming chamber 630 and the methanic chamber 640 to allow liquid waste to plug flow from the acid forming chamber 630 into the methanic chamber 640. The acid forming chamber 630 used to treat alkaline liquid waste is typically larger than the acid forming chambers used to treat acidic liquid waste. In some embodiments, the acid forming chamber 630 is about four times larger that those used to treat acidic liquid waste.

As the liquid waste flows through the acid forming chamber 630, acid forming bacteria convert complex carbon molecules into simpler acids. As a result, the pH of the liquid waste in the acid forming chamber 630 is lowest at the downstream end 630b and highest at the upstream end 630a. A pH monitoring station E in the acid forming chamber 630 measures the pH of the influent liquid waste. When the pH of the influent waste becomes too high to support the acid forming bacteria, liquid waste from the downstream end 630b of the acid forming chamber 630 is recycled via flow path 693 to the upstream end 630a of the acid forming chamber 630 to reduce the pH of the influent alkaline liquid waste. The flow path 693 may be defined by any number of devices that may include, but are not limited to, a pipe, tile, a channel, and a tube. In some embodiments, the pH monitoring station E triggers a vari-speed recirculation pump. The pump recycles an appropriate amount of liquid waste from the downstream end 630b of the acid forming chamber 630 to the upstream end 630a of the acid forming chamber 630 to adjust the influent alkaline liquid waste to a neutral pH of about 6.5 to about 7.5.

The recirculation of the lower pH liquid waste enables the waste treatment system 610 to self-regulate the pH of the influent liquid waste to a level that is within the range of bacteria acceptance and reduce or eliminate the need for outside acid addition. This recirculation of the lower pH liquid waste also serves to reseed liquid waste at the upstream end 630a of the acid forming chamber 630 with acid forming bacteria. Reseeding may increase bacterial action on liquid waste, particularly bacteria sterile influent wastes, such as glycerin waste. The amount of liquid waste recycled from the downstream end 630b of the acid forming chamber 630 to the upstream end 630a of the acid forming chamber 630 will be reflected in the increased hydraulic retention time sizing of the acid portion of the waste treatment system 610. The liquid waste, upon entering the methanic chamber 640, contains the proper pH and simple acid components for efficient conversion into methane biogas and the reduction of organic compounds, and will be processed in the established pattern of the waste treatment system 610.

The acid forming chamber 630 includes a heating device 622 for heating the liquid waste as it flows through the acid forming chamber 630. The heating device 622 may, for example, be a heating conduit (not shown) or other conduit containing a liquid or gas. The heating 622 device may include discharge nozzles to further agitate the liquid waste.

The liquid waste from the acid forming chamber 630 is transferred via horizontal plug-flow movement of the liquid waste to the methanic chamber 640. As shown in FIG. 9, the methanic chamber 640 may be a U-shaped tank. A center wall 665 divides the methanic chamber 640 into a first leg or passageway 646 and second leg or passageway 648 of the U-shape. The liquid waste moves from the acid forming chamber 630 into the methanic chamber 640 along the first leg 646 in a first direction, and toward the sludge pit 660 along the second leg 648 of the methanic chamber 640 in a second direction opposite the first direction.

One or more partitions 670 may run severally parallel to, and on opposite sides of, the center wall 665. The partitions 670 may comprise at least one of a rigid board or plank, curtain or drape, tarp, film, and a combination thereof. In addition, the partitions 670 may be constructed of a variety of materials including, without limitation, at least one of metal, wood, polymer, ceramic, composite, and a combination thereof. The partitions 670 are shorter than the center wall 665 and are raised off the floor of the methanic chamber 640. This allows liquid waste to flow underneath and then over the partitions 670 as it plug flows through the methanic chamber 640.

The methanic chamber 640 illustrated in FIG. 9 may include any of the features discussed with respect to the previous embodiments illustrated in FIGS. 1-7. For example, pH monitoring stations B-D may adjust the pH of the liquid waste in the methanic chamber 640 by recycling alkaline sludge from the sludge pit 660 via one or more flow paths 644.

Additionally, the methanic chamber 640 may include a heating device 672 located within the methanic chamber 640 and adjacent to the center wall 665 to maintain the liquid waste at a temperature that facilitates bacterial activity. The heating device 672 locally heats the liquid waste using, for example, hot water or gas, causing the heated mixed liquid waste to rise under convective forces. The convective forces cause the heated liquid waste to rise up the center wall 665. At the same time, liquid waste near the relatively cooler outer wall 654 falls under convective forces. As a result, the convective forces cause the liquid waste to follow a circular flow path through the first and second legs 646, 648 upward along the center wall 665 and downward along the outer wall 654. At the same time, the liquid waste flows along the first and second legs 646, 648, resulting in a combined corkscrew-like flow path for the liquid waste. The heating device 672 may include heating conduits having jet nozzles to dispense water or gas into the liquid waste. In another embodiment, hot gas injection jets using heated gases from the output of the engine (not shown) replace the hot water heating conduits as a heating and current-generating source. The injection of hot gases circulates the liquid waste through both natural and forced convection. A similar corkscrew-like flow path is thereby developed in the methanic chamber 640. In a further embodiment, at least one conduit containing compressed, recycled biogas is used in combination with the heating device 672. The compressed biogas contained in the conduit is forced out of the conduit and propelled upwardly between the conduits 670 and center wall 665 to promote the liquid waste to move upwardly through the principle of air/water lifting. The released gas may also facilitate the corkscrew-like flow path of liquid waste through the methanic chamber 640.

In operation of the waste treatment system 610, as illustrated in FIG. 9, alkaline liquid waste is transported to the waste treatment site. Prior to entering the acid forming chamber 630, the pH of the liquid waste influent may optionally be adjusted to a range of between about 6.0 and about 7.0 to start the acid forming bacterial growth. In one embodiment, a pH probe that controls a vari-speed chemical feed pump is utilized to monitor and adjust the initial pH of the influent. Agents used to adjust the pH may include a variety of acidic substances, such as industrial acids (e.g., $H_2SO_4$), acidic liquid animal wastes, or acidic organic liquid wastes.

The liquid waste enters the acid forming chamber 630 via the influent conduit 618. In the acid forming chamber 630, the internal heating device 622 adjusts the temperature of the influent to facilitate the growth of acid forming bacteria. Temperature control is important for methanogenic bacteria (less so for acid forming bacteria). The temperature is closely regulated in the acid forming chamber 630 so that the temperature is kept constant as the liquid "plug flows" from the acid forming chamber 630 into the methanic chamber 640. The temperature can be site determined to be about 97° F. to about 103° F. for a mesophilic operating digester or about 132° F. to about 138° F. for a thermophilic digester. The liquid waste in the acid forming chamber 630 is continuously stirred to eliminate temperature stratification in the liquid waste and to promote better bacterial growth. In one embodiment, the contents of the acid forming chamber are continuously stirred with recycled biogas agitation.

Within the acid forming chamber 30, acid forming bacteria convert complex carbon molecules into simpler acids. These acids in turn lower the pH of the liquid waste in the acid forming chamber 30. As a result, the pH of the liquid waste at the downstream end 630b of the acid forming chamber 630 is lower than the pH of the influent liquid waste at the upstream end 630a of the acid forming chamber 630. In some embodiments, the pH of the liquid waste at the downstream end 630*b* of the acid forming chamber 630 is about 6.0.

A pH monitoring station E measures the pH of influent alkaline waste as it enters the upstream end 630*a* of the acid forming chamber 630. If the pH of the influent liquid waste is greater than about 7, an appropriate amount of liquid waste from the downstream end 630*b* of the acid forming chamber 630 is recycled to the upstream end 630*a* of the acid forming chamber to reduce the pH of the influent liquid waste to about neutral. This insures that the pH of the influent liquid waste will be maintained at a level that fosters acid-forming bacteria growth rates and efficiency. In some embodiments, a roof mounted pH monitor identified by pH monitoring station E controls a vari-speed sludge recirculation pump to recycle liquid waste from the downstream end 630*b* to the upstream end 630*a* of the acid forming chamber 630.

As new influent enters the acid forming chamber 630, the treated liquid waste within the acid forming chamber 630 will plug flow into the methanic chamber 640. In the methanic chamber 640, an environment to foster the growth of the methanogenic bacteria is maintained. The pH of the liquid waste in the methanic chamber 640 is maintained at a pH of about 6.5 to about 8.0, and particularly at a pH of about 7.5 to about 8.0. To accomplish this, pH monitoring stations (B-D) are located throughout the methanic chamber 640. If the pH drops below a set value, such as 6.5, at any of these stations, the pH monitors will activate one or more vari-speed sludge recirculation pumps to add alkaline sludge from the sludge pit 660 to the liquid waste in the methanic chamber 640. The corkscrew mixing of the liquid waste in the methanic chamber 640 by the utilization of the recirculated biogas and/or heating ensures a homogeneous pH mix and prevents pH stratification within the vessel. A heating device 672 within the methanic chamber 640 maintains the temperature of the liquid waste within a range of about 1 to about 2 degrees of the set point temperature. The set point temperature for a mesophilic temperature digester will be about 100° F. and about 134° F. for a thermophilic digester. The heating device 672 can be utilized for heating or cooling as determined by the influent liquid temperature. The liquid waste within the methanic chamber 640 is continuously mixed with recycled biogas jetted into the liquid waste in a direction perpendicular to the waste flow direction. Mixing prevents stratification within the methanic chamber and enhances biodegradation.

As the waste stream plug flows through the methanic chamber 640, it is allowed to biodegrade in multiple sections as it travels in a horizontal corkscrew-like pathway through the first leg 646 and the second leg 648 of the methanic chamber 640. In one embodiment, the waste stream is not mixed with the newer incoming waste material. As the methanogenic bacteria function, they consume the acids created in the acid forming chamber 630 and effectively raise the pH of the liquid waste stream and increase the alkalinity of the liquid waste. At the end of the methanic chamber 640, with properly engineered hydraulic retention times based on influent characteristics, the acid forming bacteria will have long completed their function and the methanogenic bacteria will have consumed the bacteria-produced acids. This results in a waste effluent of high pH and alkalinity in comparison to the liquid waste exiting the acid forming chamber 630. The greatest alkalinity and bacteria population at the very end of the waste treatment system 610 will be in the bacteria "sludge" that is allowed to settle in the sludge pit 660 located at the end of the waste treatment system 610. The sludge pit 660 may not have mixing and thus the sludge is allowed to settle to the bottom. This sludge, with its higher alkalinity, pH, and bacteria population, is the recirculated sludge utilized at the various points (stations B, C and D) throughout the waste treatment system 610 for pH control and bacterial seeding.

The waste treatment system 610 will treat alkaline liquid wastes with a solids percentage varying between about 5 and about 40%. It does this by monitoring and closely controlling the pH in the liquid waste and by utilizing the naturally generated alkalinity and pH rise associated with the two-step anaerobic biodegradation process of acid forming bacteria followed by methanogenic bacteria and their resultant biological waste products. Use of a mixed plug flow is preferred. Additionally, the plug-flow separation of the processed wastes over the designed hydraulic retention time enables the natural increase in pH and alkalinity, thus allowing for the production of the returned sludge. Mixing of the plug flow prevents stratification in the acid forming chamber 630 and methanic chamber 640. Eliminating stratification in the acid forming chamber 630 and methanic chamber 640 prevents buildup of acid forming bacteria colonies and the resultant high acidic liquid (low pH) "dead" spots, facilitates better methanogenic bacteria growth to achieve better and faster acid neutralization and alkalinity production, and provides for more uniform hydraulic retention time in the waste treatment system 610 by preventing "short circuiting" of the liquid path flow.

The biodegraded effluent may be further treated or disposed of by the generating facility as required. Biogas generated by the anaerobic biological process may be collected in the gas collection space above the liquid level and under the ceiling of the methanic chamber 640. The biogas may be utilized as a "BTU replacement" in the production of electricity or natural gas.

Although the above embodiment was described in the context of treating alkaline liquid wastes, it should be understood by those skilled in the art the same embodiment may also be used to treat high-strength organic liquid wastes having an influent pH of about 7.

Thus, the invention provides, among other things, a system and method for treating high-strength organic liquid wastes. Various features and advantages of the invention are set forth in the following claims.

What is claimed is:

1. A system for treating liquid waste comprising:
   an acid forming chamber that at least partially converts carbon molecules in the liquid waste to acids, wherein the liquid waste is acidic high-strength organic liquid wastes, neutral high-strength organic liquid wastes, or a combination thereof;
   a plug-flow methanic chamber downstream from the acid forming chamber that at least partially converts the acids in the liquid waste to methane;
   a solid-liquid separator downstream from the methanic chamber, the separator separating a portion of the liquid waste into alkaline sludge and effluent;
   and a first flow path that recycles alkaline sludge to at least one of the acid forming chamber, the methanic chamber, and combination thereof.

2. The system of claim 1, further comprising a pH monitoring station upstream of the acid forming chamber that adjusts the pH of the liquid waste before it enters the acid forming chamber.

3. The system of claim 1, wherein the acid forming chamber contains acid forming bacteria selected from at least one of *Clostridia, Fibrobacter succinogenes, Ruminococcus albus, Butyrivibrio fibrisolvens, Selenomonas ruminatium, Streptococcuslovis, Eubacterium ruminatium*, external enzymes, and combinations thereof.

4. The system of claim 1, wherein the methanic chamber contains methanogenic bacteria selected from at least one of *Methanothrix, Methanosarcina, Methanospirillum, Methanobacterium, Methanococcus, Methanobrevibacter, Methanomicrobiummobile, Methanosaeta, Methanobacterium thermoautotrophicum, Methanobacterium formicicum, Methanobacterium thermoalcaliphilum, Methanococcus thermolithotrophicus, Methanosarcina thermophila, Methanosaela thermoacetophila*, and combinations thereof.

5. The system of claim 1, wherein the plug-flow methanic chamber may comprise a first leg having one end adjacent to the acid forming chamber and a second leg parallel to the first leg, wherein the first leg and the second leg are partially separated by a wall and the liquid waste in the first leg travels in a direction opposite to that of liquid waste in the second leg.

6. The system of claim 5, wherein the second leg is horizontally beside the first leg.

7. The system of claim 5, further comprising a heating device positioned in at least a portion of one of the first leg and the second leg to heat the liquid waste that comes in contact with the heating device to cause thermal mixing of the liquid waste.

8. The system of claim 5, further including a conduit having gas outlets in at least a portion of the first leg and the second leg to emit gas into the liquid waste to cause mixing of the waste.

9. The system of claim 1, wherein the liquid waste follows a corkscrew-like flow path through the methanic chamber.

10. The system of claim 1, further comprising a pH probe located in one of the acid forming chamber, the methanic chamber, or combination thereof; and a recirculation pump that is activated by the pH probe to recycle alkaline sludge to one of the acid forming chamber, the methanic chamber, or combination thereof.

11. The system of claim 1, wherein the methanic chamber further comprises one or more walls and a partition positioned relative thereto such that a space is created therebetween, and a heating device position within the space for heating the liquid waste.

12. The system of claim 1, wherein the system is anaerobic.

13. The system of claim 1, wherein the system is defined by a relatively circular outer wall.

14. The system of claim 1, wherein the first flow path recycles alkaline sludge to the methanic chamber.

15. The method of claim 14, wherein a second flow path for recycling liquid waste from a downstream end of the acid forming chamber to an upstream end of the acid forming chamber.

16. A method for treating liquid waste comprising:
converting carbon molecules within the liquid waste to acids in an acid forming chamber containing acid forming bacteria, wherein the liquid waste is acidic high-strength organic liquid wastes, neutral high-strength organic liquid wastes, or a combination thereof;
converting the acids in the liquid waste from the acid forming chamber into methane in a methanic chamber containing methanogenic bacteria;
separating the liquid waste from the methanic chamber into alkaline sludge and effluent; and
recycling at least a portion of the alkaline sludge to one of the acid forming chamber, methanic chamber, or combination thereof.

17. The method of claim 16, further comprising feeding liquid waste into the acid forming chamber, the liquid waste having a pH less than about 5.0 and a solids content greater than about 5%.

18. The method of claim 16, further comprising adjusting the pH of the liquid waste to about 6.0 to about 7.0 before feeding the liquid waste into the acid forming chamber.

19. The method of claim 16, wherein the acid forming chamber contains acid forming bacteria selected from at least one of *Clostridia, Fibrobacter succinogenes, Ruminococcus albus, Butyrivibrio fibrisolvens, Selenomonas ruminatium, Streptococcuslovis, Eubacterium ruminatium*, external enzymes, and combinations thereof.

20. The method of claim 16, wherein the alkaline sludge is used to maintain the liquid waste within the acid forming chamber at a pH of about 6.0 to about 7.0.

21. The method of claim 16, wherein the liquid waste within the acid forming chamber is maintained at a temperature of about 97° F. to about 103° F.

22. The method of claim 16, wherein the liquid waste within the acid forming chamber is maintained at a temperature of about 132° F. to about 138° F.

23. The method of claim 16, wherein the methanic chamber contains methanogenic bacteria selected from at least one of *Methanothrix, Methanosarcina, Methanospirillum, Methanobacterium, Methanococcus, Methanobrevibacter, Methanomicrobiummobile, Methanosaeta, Methanobacterium thermoautotrophicum, Methanobacterium formicicum, Methanobacterium thermoalcaliphilum, Methanococcus thermolithotrophicus, Methanosarcina thermophila, Methanosaela thermoacetophila* and combinations thereof.

24. The method of claim 16, wherein the alkaline sludge is used to maintain the liquid waste within the methanic chamber at a pH of about 6.5 to about 8.0.

25. The method of claim 16, wherein the liquid waste within the methanic chamber is maintained at a temperature of about 98° F. to about 102° F.

26. The method of claim 16, wherein the liquid waste within the methanic chamber is maintained at a temperature of about 132° F. to about 136° F.

27. The method of claim 16, wherein the liquid waste follows a corkscrew-like flow path through the methanic chamber.

28. The method of claim 27, wherein a partition positioned relative to a wall of the methanic chamber facilitates the corkscrew-like flowpath.

29. The method of claim 16, wherein the converting steps in the acid forming chamber and the methanic chamber are done under anaerobic conditions.

30. The method of claim 16, wherein the liquid waste plug-flows through the methanic chamber.

31. The method of claim 16, wherein the recycling step adjusts the pH of the liquid waste during the converting steps using acid forming and methanogenic bacteria.

32. A closed anaerobic digester for digesting liquid waste comprising: a first section positioned to receive liquid waste comprising organic molecules and to convert at least a portion of the carbon molecules within the liquid waste to acids, wherein the liquid waste is acidic high-strength organic liquid wastes, neutral high-strength organic liquid wastes, or a combination thereof; a second section positioned to receive a portion of the liquid waste from the first section, the second section having one or more walls and converting at least a portion of the acids in the liquid waste to methane, the second section having a first passage and at least one second passage, wherein the waste material changes direction upon flowing from the first passage to the at least one second passage; a third section positioned to receive a portion of the liquid waste from the second section and to separate the liquid waste into an effluent and an alkaline sludge; and a flow path positioned to deliver at least a portion of the alkaline sludge to at least one of the first section, the second section and combination thereof.

33. The digester of claim 32, further comprising a partition positioned relative to the one or more walls such that a space is created there between, and wherein a heating device is positioned within the space for heating the waste material and enabling heated liquid waste to flow upwardly within the space.

34. The digester of claim 33, wherein the partition has a top edge over which heated waste material moves out of the space.

35. The digester of claim 33, wherein the partition has a bottom edge under which waste material moves into the space.

36. The digester of claim 32, further comprising a partition having a top edge and a bottom edge, the top edge being spaced a distance from a top of the closed second section, and the bottom edge being spaced a distance from a bottom of the closed second section.

37. The digester of claim 32, further comprising a fourth section adjacent to and upstream of the first section to adjust the pH of the liquid waste before the liquid waste enters the first section.

38. The digester of claim 32, wherein the first passage and the second passage are positioned to create a flow path that is generally U-shaped.

39. The digester of claim 32, wherein the liquid waste flows through the second section in a corkscrew-like flow path.

40. The digester of claim 32, further including a heating device adjacent to one or more of the walls in the second section to cause thermal mixing of the waste.

41. The digester of claim 32, further including a conduit in the second section having a gas outlet to emit gas into the liquid waste to cause mixing of the liquid waste.

42. The digester of claim 32, wherein the digester has an outer wall that is relatively circular.

43. A method for treating liquid waste comprising:
converting carbon molecules within the liquid waste to acids in an acid forming chamber containing acid forming bacteria, wherein the acid forming chamber has a downstream end and an upstream end, and further wherein the liquid waste is one of alkaline high-strength organic liquid wastes, neutral high-strength organic liquid wastes, or a combination thereof;
recycling at least a portion of the liquid from the downstream end of the acid forming chamber to the upstream end; and
converting the acids in the liquid waste from the acid forming chamber into methane in a methanic chamber containing methanogenic bacteria.

44. The method of claim 43, further comprising separating the liquid waste from the methanic chamber into alkaline sludge and effluent and recycling the alkaline swage into the methanic chamber.

45. The method of claim 44, wherein a sufficient amount of sludge is recycled to the methanic chamber to maintain the liquid waste within the methanic chamber at a pH of about 6.5 to about 8.0.

46. The method of claim 43, further comprising feeding liquid waste into the acid forming chamber, the liquid waste having a pH greater than about 8.0 and a solids content greater than about 5%.

47. The method of claim 43, further comprising adjusting the pH of the liquid waste to about 6.0 to about 7.0 before feeding the liquid waste into the acid forming chamber.

48. The method of claim 43, wherein the acid forming chamber contains acid forming bacteria selected from at least one of *Clostridia, Fibrobacter succinogenes, Ruminococcus albus, Butyrivibrio fibrisolvens, Selenomonas ruminatium, Streptococcuslovis, Eubacterium ruminatium*, external enzymes, and combinations thereof.

49. The method of claim 43, wherein recycling the liquid waste from the downstream end of the acid forming chamber to the upstream end of the acid forming chamber maintains the liquid waste at the upstream end of the acid forming chamber at a pH of about 6.5 to about 7.5.

50. The method of claim 43, wherein the liquid waste within the acid forming chamber is maintained at a temperature of about 97° F. to about 103° F.

51. The method of claim 43, wherein the liquid waste within the acid forming chamber is maintained at a temperature of about 132° F. to about 138° F.

52. The method of claim 43, wherein the methanic chamber contains methanogenic bacteria selected from at least one of *Methanothrix, Methanosarcina, Methanospirillum, Methanobacterium, Methanococcus, Methanobrevibacter, Methanomicrobiummobile, Methanosaeta, Methanobacterium thermoautotrophicum, Methanobacterium formicicum, Methanobacterium thermoalcaliphilum, Methanococcus thermolithotrophicus, Methanosarcina thermophila, Methanosaela thermoacetophila*, and combinations thereof.

53. The method of claim 43, wherein the liquid waste within the methanic chamber is maintained at a temperature of about 98° F. to about 102° F.

54. The method of claim 43, wherein the liquid waste within the methanic chamber is maintained at a temperature of about 132° F. to about 136° F.

55. The method of claim 43, wherein the liquid waste follows a corkscrew-like flow path through the methanic chamber.

56. The method of claim 55, wherein a partition positioned relative to a wall of the methanic chamber facilitates the corkscrew-like flow path.

57. The method of claim 43, wherein the converting steps in the acid forming chamber and the methanic chamber are done under anaerobic conditions.

58. The method of claim 43, wherein the liquid waste plug-flows through the methanic chamber.

59. A closed anaerobic digester for digesting liquid waste comprising: a first section having an upstream end and a downstream end positioned to receive liquid waste comprising organic molecules and to convert at least a portion of the organic molecules within the liquid waste to acids, wherein the liquid waste is acidic high-strength organic liquid wastes, neutral high-strength organic liquid wastes, or a combination thereof; a second section positioned to receive a portion of the liquid waste from the first section, the second section having one or more walls and converting at least a portion of the acids in the liquid waste to methane, the second section having a first passage and at least one second passage, wherein the waste material changes direction upon flowing from the first passage to the at least one second passage; a third section positioned to receive a portion of the liquid waste from the second section and to separate the liquid waste into an effluent and an alkaline sludge; and a first flow path for recycling liquid waste from the downstream end to the upstream end of the first section.

60. The digester of claim 59, further comprising a partition positioned relative to the one or more walls such that a space is created therebetween, and wherein a heating device is positioned within the space for heating the waste material and enabling heated waste material to flow upwardly within the space.

61. The digester of claim 60, wherein the partition has a top edge over which heated waste material moves out of the space.

62. The digester of claim 60, wherein the partition has a bottom edge under which waste material moves into the space.

63. The digester of claim 60, further comprising a fourth section adjacent to and upstream of the first section to adjust the pH of the liquid waste before it enters the first section.

64. The digester of claim 60, wherein the first passage and the second passage are positioned to create a flow path that is generally U-shaped.

65. The digester of claim 60, wherein the liquid waste flows through the second section in a corkscrew-like flow path.

66. The digester of claim 60, further including a heating device adjacent to one or more of the walls in the second section to cause thermal mixing of the waste.

67. The digester of claim 60, further comprising a flow path positioned to deliver at least a portion of the alkaline sludge from the third section to the second section.

* * * * *